United States Patent
Lönnroth et al.

(10) Patent No.: US 6,344,440 B1
(45) Date of Patent: Feb. 5, 2002

(54) ANTISECRETORY FACTOR PEPTIDES REGULATING PATHOLOGICAL PERMEABILITY CHANGES

(75) Inventors: Ivar Lönnroth, Mölndal; Stefan Lange, Göteborg; Eva Johansson, Mölndal; Eva Jennische, Göteborg; Christina Lönnroth, Mölndal, all of (SE)

(73) Assignee: Rural Patent Svenska AB, Stockholm (SE)

( * ) Notice: Subject to any disclaimer, the term of this patent is extended or adjusted under 35 U.S.C. 154(b) by 0 days.

(21) Appl. No.: 09/029,333

(22) PCT Filed: Aug. 23, 1996

(86) PCT No.: PCT/SE96/01049

§ 371 Date: Mar. 13, 1998

§ 102(e) Date: Mar. 13, 1998

(87) PCT Pub. No.: WO97/08202

PCT Pub. Date: Mar. 6, 1997

(30) Foreign Application Priority Data

Aug. 24, 1995 (SE) ................................................ 9502936

(51) Int. Cl.$^7$ ............................................... C07K 14/00

(52) U.S. Cl. ........................... 514/12; 530/350; 530/300

(58) Field of Search ................................. 530/350, 324, 530/328, 327, 326; 514/2, 12, 13, 14, 15, 16; 424/198.1, 200.1; 426/635, 656; 435/69.1, 252.3, 320.1; 800/4

(56) References Cited

PUBLICATIONS

Database GenBank on STN, Accession No. S79502, Haracska et al. (1995).*
Database GenBank on STN, Accession No. T24435, Matsubara et al. (Jun. 1, 1995).*
Lonnroth et al. (1986) Biochimica et Biophysica Acta, 883, pp. 138–144.*
Johansson et al. (Sep. 1995) J. Biol. Chem. 270/35, pp. 20615–20620.*
Hansen et al. (1995) Physiol. Res. 44:61–78.*
"Efficient Isolation of Genes by Using Antibody Probes", Richard A. Young and Ronald W. Davis, Proc. Natl. Acad. Sci. USA, vol. 80, Mar. 1983, pp. 1194–1198.
*Molecular Cloning: A Laborarory Manual*, J. Sambrook, E.F. Fritsch, T. Maniatis, Cold Spring Harbor Laboratory Press, 1989, pp. 1.74–1.84.
"Rapid Production of Full–Length cDNAs From Rare Transcripts: Amplification Using a Single Gene–Specific Oligonucleotide Primer", Michael A. Frohman, Michael K. Dush, Gail R. Martin, Proc. Natl. Acad. Sci. USA, vol. 85, Dec. 1988, pp. 8998–9002.

"Cleavage of Structural Proteins During the Assembly of the Head of Bacteriophage T4", U.K. Laemmli, Nature, vol. 227, Aug. 15, 1970, pp. 680–685.
"An Enzyme–Linked–Immunosorbent Assay Method for Detection of Immunoglobulins to Pertussis Toxin", G. Zackrission, T. Lagergard, and I. Lönnroth, Acta path. microbiol. immunol. scand. Sect. C, 94, pp. 227–231, 1986.
"Single–Step Method of RNA Isoloation by Acid Guanidinium Thiocyantate–Phenol–Chloroform Extraction", P. Chomczynski and N. Sacchi, Analytical Biochemistry 162, 1987, pp. 156–159.
*Molecular Cloning: A Laborartory Manual*, J. Sambrook, E.F. Fritsch, T. Maniatis, Cold Spring Harbor Laboratory Press, 1989, pp. 7.40–7.42.
"IGF–I Binding and IGF–I Expression in Regenerating Muscle of Normal and Hypophysectomized Rats", E. Jennische and G.L. Matejka, Acta Physiol Scand 1992, 146, pp. 79–86.
"Passive Transfer of Protection Against Cholera Toxin in Rat Intestine", Stefan Lange and Ivar Lönnroth, FEMS Microbiology Letters 24, 1984, pp. 165–168.
"Enterotoxins from *Clostridium difficile*; Diarrhoeogenic Potency and Morphological Effects in the Rat Intestine", J. Torres, E. Jennische, S. Lange, I. Lönnroth Gut, 1990, pp. 781–785.
"Evans Blue Permeation of Intestinal Mucosa in the Rat", S. Lange, D. S. Delbro & E. Jennische, Scand J. Gastroenterol 1994, pp. 29, 38–46.
"The Antisecretory Factors: Inducible Proteins Which Modulate Secretion in the Small Intestine", Comp. Biochem. Physiol, vol. 90A, No. 4, 1998, pp. 611–617.
"New Aspects of the Pathophysiology and Treatment of Secretory Diarrhoea", Physiol Res., vol. 44, 1995, M.B. Hansen et al., pp. 61–78.

* cited by examiner

Primary Examiner—Karen Cochrane Carlson
(74) Attorney, Agent, or Firm—Burns, Doane, Swecker & Mathis, L.L.P.

(57) ABSTRACT

A new recombinant protein called Antisecretory Factor (rAF) and homologues and peptide fragments thereof are described. The protein and the homologues and fragments thereof are useful for normalizing pathological fluid transport and/or inflammatory reactions in animals including humans. Antibodies against AF or homologues or fragments thereof are described. Nucleic acids coding for the protein or for homologues or fragments thereof are also described as well as vectors and hosts comprising the nucleic acids. The rAF and homologues and fragments thereof could be used for immunodetection, as feed additive for growing animals and as antidiarrheal and drugs against diseases involving edema, dehydration and/or inflammation.

23 Claims, 12 Drawing Sheets

FIG. 1A

AATTGGAGGAGTTGTTGTTAGGCCGTCCCGGAGACCCGGTCGGGAGGGAG

Figure 1C:
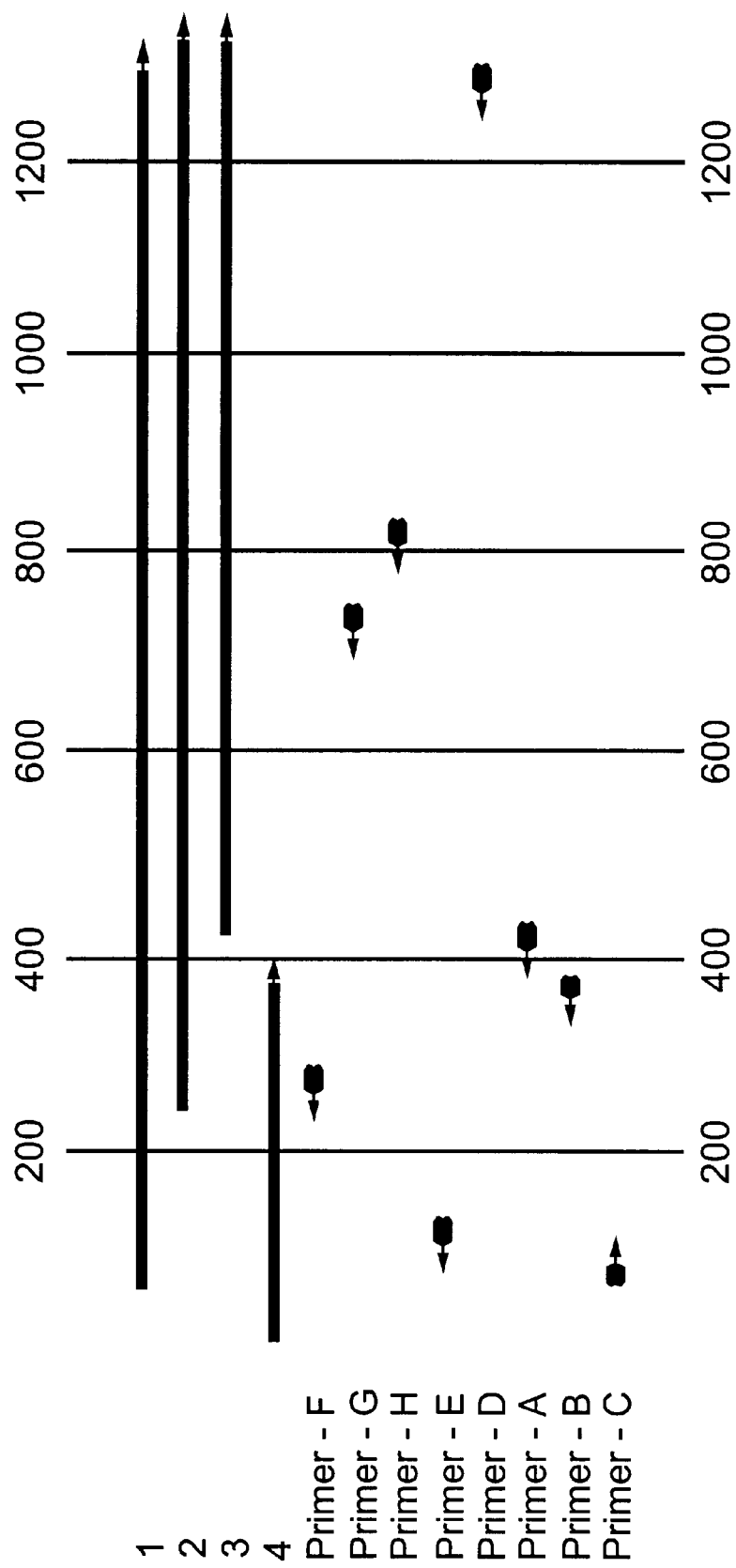

| | | | | | | | | | | | | |
|---|---|---|---|---|---|---|---|---|---|---|---|---|
| GAAGGTGGCAAG | ATG | GTG | TTG | GAA | AGC | ACT | ATG | GTG | TGT | GTG | GAC | AAC AGT 101 |
| | Met | Val | Leu | Glu | Ser | Thr | Met | Val | Cys | Val | Asp | Asn Ser> |
| | | | | 5 | | | | | 10 | | | |

| | | | | | | | | | | | |
|---|---|---|---|---|---|---|---|---|---|---|---|
| GAG | TAT | ATG | CGG | AAT | GGA | GAC | TTC | TTA | CCC | ACC | AGG CTG CAG GCC CAG 149 |
| Glu | Tyr | Met | Arg | Asn | Gly | Asp | Phe | Leu | Pro | Thr | Arg Leu Gln Ala Gln> |
| | 15 | | | | 20 | | | | 25 | | |

CAG GAT GCT GTC AAC ATA GTT TGT CAT TCA AAG ACC CGC AGC AAC CCT 197
Gln Asp Ala Val Asn Ile Val Cys His Ser Lys Thr Arg Ser Asn Pro>
30              35              40              45

GAG AAC AAC GTG GGC CTT ATC ACA CTG GCT AAT GAC TGT GAA GTG CTG 245
Glu Asn Asn Val Gly Leu Ile Thr Leu Ala Asn Asp Cys Glu Val Leu>
        50              55              60

ACC ACA CTC ACC CCA GAC ACT GGC CGT ATC CTG TCC AAG CTA CAT ACT 293
Thr Thr Leu Thr Pro Asp Thr Gly Arg Ile Leu Ser Lys Leu His Thr>
        65              70              75

GTC CAA CCC AAG GGC AAG ATC ACC TTC TGC ACG GGC ATC CGC GTG GCC 341
Val Gln Pro Lys Gly Lys Ile Thr Phe Cys Thr Gly Ile Arg Val Ala>
        80              85              90

CAT CTG GCT CTG AAG CAC CGA CAA GGC AAG AAT CAC AAG ATG CGC ATC 389
His Leu Ala Leu Lys His Arg Gln Gly Lys Asn His Lys Met Arg Ile>
    95              100             105

ATT GCC TTT GTG GGA AGC CCA GTG GAG GAC AAT GAG AAG GAT CTG GTG 437
Ile Ala Phe Val Gly Ser Pro Val Glu Asp Asn Glu Lys Asp Leu Val>
110             115             120             125

AAA CTG GCT AAA CGC CTC AAG AAG GAG AAA GTA AAT GTT GAC ATT ATC 485
Lys Leu Ala Lys Arg Leu Lys Lys Glu Lys Val Asn Val Asp Ile Ile>
        130             135             140

AAT TTT GGG GAA GAG GAG GTG AAC ACA GAA AAG CTG ACA GCC TTT GTA 533
Asn Phe Gly Glu Glu Glu Val Asn Thr Glu Lys Leu Thr Ala Phe Val>
        145             150             155

AAC ACG TTG AAT GGC AAA GAT GGA ACC GGT TCT CAT CTG GTG ACA GTG 581
Asn Thr Leu Asn Gly Lys Asp Gly Thr Gly Ser His Leu Val Thr Val>
        160             165             170

CCT CCT GGG CCC AGT TTG GCT GAT GCT CTC ATC AGT TCT CCG ATT TTG 629
Pro Pro Gly Pro Ser Leu Ala Asp Ala Leu Ile Ser Ser Pro Ile Leu>
    175             180             185

FIG. 1B

```
GCT GGT GAA GGT GGT GCC ATG CTG GGT CTT GGT GCC AGT GAC TTT GAA   677
Ala Gly Glu Gly Gly Ala Met Leu Gly Leu Gly Ala Ser Asp Phe Glu>
190             195             200             205

TTT GGA GTA GAT CCC AGT GCT GAT CCT GAG CTG GCC TTG GCC CTT CGT   725
Phe Gly Val Asp Pro Ser Ala Asp Pro Glu Leu Ala Leu Ala Leu Arg>
        210             215             220

GTA TCT ATG GAA GAG CAG CGG CAC GCA GGA GGA GGA GCG CGG CGG GCA   773
Val Ser Met Glu Glu Gln Arg His Ala Gly Gly Gly Ala Arg Arg Ala>
            225             230             235

GCT CGA GCT TCT GCT GCT GAG GCC GGG ATT GCT ACG ACT GGG ACT GAA   821
Ala Arg Ala Ser Ala Ala Glu Ala Gly Ile Ala Thr Thr Gly Thr Glu>
        240             245             250

GAC TCA GAC GAT GCC CTG CTG AAG ATG ACC ATC AGC CAG CAA GAG TTT   869
Asp Ser Asp Asp Ala Leu Leu Lys Met Thr Ile Ser Gln Gln Glu Phe>
        255             260             265

GGC CGC ACT GGG CTT CCT GAC CTA AGC AGT ATG ACT GAG GAA GAG CAG   917
Gly Arg Thr Gly Leu Pro Asp Leu Ser Ser Met Thr Glu Glu Glu Gln>
270             275             280             285

ATT GCT TAT GCC ATG CAG ATG TCC CTG CAG GGA GCA GAG TTT GGC CAG   965
Ile Ala Tyr Ala Met Gln Met Ser Leu Gln Gly Ala Glu Phe Gly Gln>
            290             295             300

GCG GAA TCA GCA GAC ATT GAT GCC AGC TCA GCT ATG GAC ACA TCT GAG  1013
Ala Glu Ser Ala Asp Ile Asp Ala Ser Ser Ala Met Asp Thr Ser Glu>
        305             310             315

CCA GCC AAG GAG GAG GAT GAT TAC GAC GTG ATG CAG GAC CCC GAG TTC  1061
Pro Ala Lys Glu Glu Asp Asp Tyr Asp Val Met Gln Asp Pro Glu Phe>
        320             325             330

CTT CAG AGT GTC CTA GAG AAC CTC CCA GGT GTG GAT CCC AAC AAT GAA  1109
Leu Gln Ser Val Leu Glu Asn Leu Pro Gly Val Asp Pro Asn Asn Glu>
        335             340             345

GCC ATT CGA AAT GCT ATG GGC TCC CTG CCT CCC AGG CCA CCA AGG ACG  1157
Ala Ile Arg Asn Ala Met Gly Ser Leu Pro Pro Arg Pro Pro Arg Thr>
350             355             360             365

GCA AGA AGG ACA AGA AGG AGG AAG ACA AGA AGT GAG ACT GGA GGG AAA  1205
Ala Arg Arg Thr Arg Arg Arg Lys Thr Arg Ser Glu Thr Gly Gly Lys>
            370             375             380

GGG TAGCTGAGTCTGCTTAGGGGACTGCATGGGAAGCACGGAATATAGGGTTAGATGTGTGT
Gly>

TATCTGTAACCATTACAGCCTAAATAAAGCTTGGCAACTTTTAAAAAAAAAAAAAAAAAAAA
```

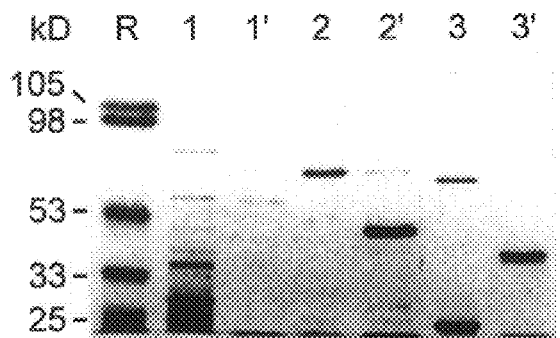 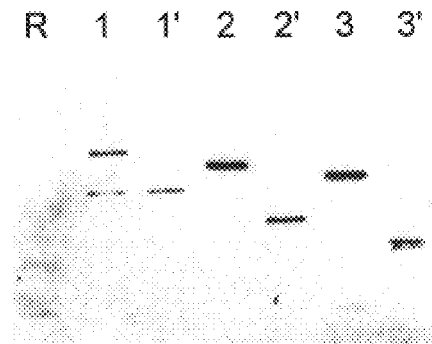
FIG. 2A          FIG. 2B
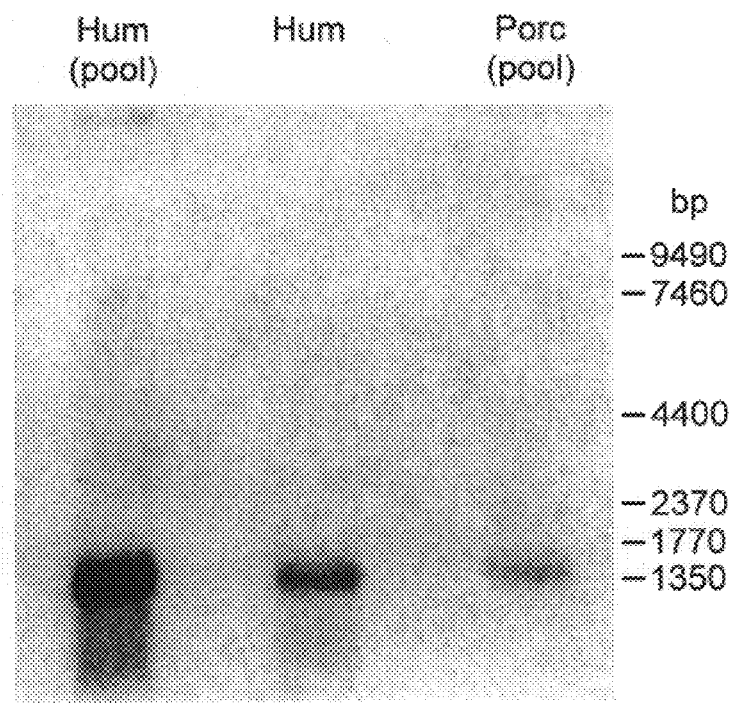
FIG. 4

SEQUENCE LISTING

```
<160> NUMBER OF SEQ ID NOS: 2

<210> SEQ ID NO 1
<211> LENGTH: 1328
<212> TYPE: DNA
<213> ORGANISM: Human
<220> FEATURE:
<221> NAME/KEY: mat_peptide
<222> LOCATION: (63)..(1208)
<220> FEATURE:
<221> NAME/KEY: sig_peptide
<222> LOCATION: (1289)..(1295)
<220> FEATURE:
<221> NAME/KEY: CDS
<222> LOCATION: (63)..(1208)

<400> SEQUENCE: 1
aattggagga gttgttgtta ggccgtcccg gagacccggt cgggagggag caaggtggca      60 ag atg gtg ttg gaa agc act atg gtg tgt gtg gac aac agt gag tat       107
   Met Val Leu Glu Ser Thr Met Val Cys Val Asp Asn Ser Glu Tyr
   1               5                  10                  15 atg cgg aat gga gac ttc tta ccc acc agg ctg cag gcc cag cag gat     155
Met Arg Asn Gly Asp Phe Leu Pro Thr Arg Leu Gln Ala Gln Gln Asp
           20                  25                  30 gct gtc aac ata gtt tgt cat tca aag acc cgc agc aac cct gag aac     203
Ala Val Asn Ile Val Cys His Ser Lys Thr Arg Ser Asn Pro Glu Asn
       35                  40                  45
```

-continued

| | | |
|---|---|---|
| aac gtg ggc ctt atc aca ctg gct aat gac tgt gaa gtg ctg acc aca<br>Asn Val Gly Leu Ile Thr Leu Ala Asn Asp Cys Glu Val Leu Thr Thr<br>50                    55                    60 | 251 |
| ctc acc cca gac act ggc cgt atc ctg tcc aag cta cat act gtc caa<br>Leu Thr Pro Asp Thr Gly Arg Ile Leu Ser Lys Leu His Thr Val Gln<br>65                    70                    75 | 299 |
| ccc aag ggc aag atc acc ttc tgc acg ggc atc cgc gtg gcc cat ctg<br>Pro Lys Gly Lys Ile Thr Phe Cys Thr Gly Ile Arg Val Ala His Leu<br>80                    85                    90                    95 | 347 |
| gct ctg aag cac cga caa ggc aag aat cac aag atg cgc atc att gcc<br>Ala Leu Lys His Arg Gln Gly Lys Asn His Lys Met Arg Ile Ile Ala<br>                  100                   105                   110 | 395 |
| ttt gtg gga agc cca gtg gag gac aat gag aag gat ctg gtg aaa ctg<br>Phe Val Gly Ser Pro Val Glu Asp Asn Glu Lys Asp Leu Val Lys Leu<br>              115                   120                   125 | 443 |
| gct aaa cgc ctc aag aag gag aaa gta aat gtt gac att atc aat ttt<br>Ala Lys Arg Leu Lys Lys Glu Lys Val Asn Val Asp Ile Ile Asn Phe<br>130                    135                   140 | 491 |
| ggg gaa gag gag gtg aac aca gaa aag ctg aca gcc ttt gta aac acg<br>Gly Glu Glu Glu Val Asn Thr Glu Lys Leu Thr Ala Phe Val Asn Thr<br>              145                   150                   155 | 539 |
| ttg aat ggc aaa gat gga acc ggt tct cat ctg gtg aca gtg cct cct<br>Leu Asn Gly Lys Asp Gly Thr Gly Ser His Leu Val Thr Val Pro Pro<br>160                    165                   170                   175 | 587 |
| ggg ccc agt ttg gct gat gct ctc atc agt tct ccg att ttg gct ggt<br>Gly Pro Ser Leu Ala Asp Ala Leu Ile Ser Ser Pro Ile Leu Ala Gly<br>                  180                   185                   190 | 635 |
| gaa ggt ggt gcc atg ctg ggt ctt ggt gcc agt gac ttt gaa ttt gga<br>Glu Gly Gly Ala Met Leu Gly Leu Gly Ala Ser Asp Phe Glu Phe Gly<br>              195                   200                   205 | 683 |
| gta gat ccc agt gct gat cct gag ctg gcc ttg gcc ctt cgt gta tct<br>Val Asp Pro Ser Ala Asp Pro Glu Leu Ala Leu Ala Leu Arg Val Ser<br>210                    215                   220 | 731 |
| atg gaa gag cag cgg cac gca gga gga gga gcg cgg cgg gca gct cga<br>Met Glu Glu Gln Arg His Ala Gly Gly Gly Ala Arg Arg Ala Ala Arg<br>225                    230                   235 | 779 |
| gct tct gct gct gag gcc ggg att gct acg act ggg act gaa gac tca<br>Ala Ser Ala Ala Glu Ala Gly Ile Ala Thr Thr Gly Thr Glu Asp Ser<br>240                    245                   250                   255 | 827 |
| gac gat gcc ctg ctg aag atg acc atc agc cag caa gag ttt ggc cgc<br>Asp Asp Ala Leu Leu Lys Met Thr Ile Ser Gln Gln Glu Phe Gly Arg<br>                  260                   265                   270 | 875 |
| act ggg ctt cct gac cta agc agt atg act gag gaa gag cag att gct<br>Thr Gly Leu Pro Asp Leu Ser Ser Met Thr Glu Glu Glu Gln Ile Ala<br>              275                   280                   285 | 923 |
| tat gcc atg cag atg tcc ctg cag gga gca gag ttt ggc cag gcg gaa<br>Tyr Ala Met Gln Met Ser Leu Gln Gly Ala Glu Phe Gly Gln Ala Glu<br>290                    295                   300 | 971 |
| tca gca gac att gat gcc agc tca gct atg gac aca tct gag cca gcc<br>Ser Ala Asp Ile Asp Ala Ser Ser Ala Met Asp Thr Ser Glu Pro Ala<br>305                    310                   315 | 1019 |
| aag gag gag gat gat tac gac gtg atg cag gac ccc gag ttc ctt cag<br>Lys Glu Glu Asp Asp Tyr Asp Val Met Gln Asp Pro Glu Phe Leu Gln<br>320                    325                   330                   335 | 1067 |
| agt gtc cta gag aac ctc cca ggt gtg gat ccc aac aat gaa gcc att<br>Ser Val Leu Glu Asn Leu Pro Gly Val Asp Pro Asn Asn Glu Ala Ile<br>              340                   345                   350 | 1115 |
| cga aat gct atg ggc tcc ctg cct ccc agg cca cca agg acg gca aga<br>Arg Asn Ala Met Gly Ser Leu Pro Pro Arg Pro Pro Arg Thr Ala Arg<br>              355                   360                   365 | 1163 |

```
agg aca aga agg agg aag aca aga agt gag act gga ggg aaa ggg          1208
Arg Thr Arg Arg Arg Lys Thr Arg Ser Glu Thr Gly Gly Lys Gly
        370                 375                 380 tagctgagtc tgcttagggg actgcatggg aagcacggaa tatagggtta gatgtgtgtt    1268
atctgtaacc attacagcct aaataaagct tggcaacttt taaaaaaaaa aaaaaaaaaa    1328
```

<210> SEQ ID NO 2
<211> LENGTH: 382
<212> TYPE: PRT
<213> ORGANISM: Human

<400> SEQUENCE: 2

```
Met Val Leu Glu Ser Thr Met Val Cys Val Asp Asn Ser Glu Tyr Met
1               5                   10                  15

Arg Asn Gly Asp Phe Leu Pro Thr Arg Leu Gln Ala Gln Gln Asp Ala
            20                  25                  30

Val Asn Ile Val Cys His Ser Lys Thr Arg Ser Asn Pro Glu Asn Asn
        35                  40                  45

Val Gly Leu Ile Thr Leu Ala Asn Asp Cys Glu Val Leu Thr Thr Leu
    50                  55                  60

Thr Pro Asp Thr Gly Arg Ile Leu Ser Lys Leu His Thr Val Gln Pro
65                  70                  75                  80

Lys Gly Lys Ile Thr Phe Cys Thr Gly Ile Arg Val Ala His Leu Ala
                85                  90                  95

Leu Lys His Arg Gln Gly Lys Asn His Lys Met Arg Ile Ile Ala Phe
            100                 105                 110

Val Gly Ser Pro Val Glu Asp Asn Glu Lys Asp Leu Val Lys Leu Ala
        115                 120                 125

Lys Arg Leu Lys Lys Glu Lys Val Asn Val Asp Ile Ile Asn Phe Gly
    130                 135                 140

Glu Glu Glu Val Asn Thr Glu Lys Leu Thr Ala Phe Val Asn Thr Leu
145                 150                 155                 160

Asn Gly Lys Asp Gly Thr Gly Ser His Leu Val Thr Val Pro Pro Gly
                165                 170                 175

Pro Ser Leu Ala Asp Ala Leu Ile Ser Ser Pro Ile Leu Ala Gly Glu
            180                 185                 190

Gly Gly Ala Met Leu Gly Leu Gly Ala Ser Asp Phe Glu Phe Gly Val
        195                 200                 205

Asp Pro Ser Ala Asp Pro Glu Leu Ala Leu Ala Leu Arg Val Ser Met
    210                 215                 220

Glu Glu Gln Arg His Ala Gly Gly Gly Ala Arg Arg Ala Ala Arg Ala
225                 230                 235                 240

Ser Ala Ala Glu Ala Gly Ile Ala Thr Thr Gly Thr Glu Asp Ser Asp
                245                 250                 255

Asp Ala Leu Leu Lys Met Thr Ile Ser Gln Gln Glu Phe Gly Arg Thr
            260                 265                 270

Gly Leu Pro Asp Leu Ser Ser Met Thr Glu Glu Glu Gln Ile Ala Tyr
        275                 280                 285

Ala Met Gln Met Ser Leu Gln Gly Ala Glu Phe Gly Gln Ala Glu Ser
    290                 295                 300

Ala Asp Ile Asp Ala Ser Ser Ala Met Asp Thr Ser Glu Pro Ala Lys
305                 310                 315                 320

Glu Glu Asp Asp Tyr Asp Val Met Gln Asp Pro Glu Phe Leu Gln Ser
                325                 330                 335
```

-continued

```
Val Leu Glu Asn Leu Pro Gly Val Asp Pro Asn Glu Ala Ile Arg
            340                 345                 350

Asn Ala Met Gly Ser Leu Pro Pro Arg Pro Pro Arg Thr Ala Arg Arg
            355                 360                 365

Thr Arg Arg Lys Thr Arg Ser Glu Thr Gly Gly Lys Gly
    370                 375                 380
```

ANTISECRETORY FACTOR PEPTIDES REGULATING PATHOLOGICAL PERMEABILITY CHANGES

The present invention relates to new antisecretory factors having fluid transport and/or inflammatory reactions regulating properties as well as polynucleic regulating properties, and polynucleic acids coding therefor, and the use thereof.

All cells and tissues of the body are critically dependent on a constant and normal fluid environment in combination with an adequate blood supply. Derangement of one or both of these supporting systems may rapidly become fatal. Concerning fluid imbalance, two principally different systems exist:
A. edema, which is characterised by the abnormal accumulation of fluid in the intercellular tissue spaces or body cavities, or
B. dehydration, which, in a strict sense, means loss of water only, but is in fact commonly used to describe the combined loss of water and ions.

The most common forms of either edema or dehydration are:

diarrheas, inflammatory bowel diseases, brain edema, asthma, rhinitis, conjunctivitis, arthritis, glaucoma, various forms of pathological intracranial pressure (increase or decrease), pressure alteration in the middle ear such as Morbus Meniere, dermatitis, chemical or physical derangement of the skin and skin adjacent glands such as mastitis, various forms of endocrine disorders, such as diabetes insipidus. Conn's syndrome, Cushing's syndrome and Morbus Addison, kidney diseases such as pyelonephritis and glomerulonephritis, metabolic diseases such as myxedema and acute intermittent porphyria, side effects during treatment with various drugs such as anti-diabetics, tricyclic antidepressants, cytostatics, barbiturates, narcotics and narcotic analogues.

Diarrhea is caused by a change in the permeability in the gut for electrolytes and water. This disturbance is often caused by bacterial enterotoxins such as those produced by *Escerichia coli, Campylobacter jejuni, Vibrio cholerae, Shigella dysenteriae* and *Clostridium difficile*. The disturbance could also be caused by intestinal inflammation. Since the uptake of water is coupled to the uptake of electrolytes and nutrients, animals with frequent diarrhea suffers from malnutrition, resulting in retardation of the daily weight gain in the growing animal. The body counteracts these reactions by neuro-hormonal mechanisms such as the release of somatostatin and opiate peptides from interneurons in the intestinal mucosa. These polypeptides are capable of reversing fluid secretion and diarrhea.

The recently described antisecretory factor (AF) has been partially purified from pig pituitary gland and shown to reverse pathological secretion induced by various enterotoxins. High levels of AF in sow milk protect the suckling piglets against neonatal diarrhea.

Antimicrobial drugs have been widely used in the treatment of diarrhea in both human and veterinarian medicine. They are also used as feed additives for pigs, calves and chicken. However, due to the rapid development of resistant bacteria in the gut, the use of antibiotics against enteritis is generally not accepted in human medicine and their use is also diminishing in veterinarian medicine.

Other antidiarrheal drugs counteract the secretion in the intestinal mucosa. Since these drugs are directed against the host animal, it is unlikely that resistance against the drugs will develop. These types of drugs include nerve-active drugs like phenothiazines and thioxanthenes. Due to some serious side effects these types of drugs have not been accepted for treatment of diarrhea in most countries. Other drugs are derivatives of opiates like codeine and loperamide. Since these drugs mainly acts by inhibiting intestinal mobility, they also inhibit the clearance of pathogenic bacteria from the gut and should definitely not be recommended against dysenteric bacteria or parasites. Derivatives of somatostatin have been introduced recently, but have so far a limited use due to difficulties in the administration of the drugs and possible interactions with the endocrine regulation of growth.

The antisecretory factor (AF) has so far not been used directly for treatment of diarrhea or malnutrition due to the difficulties involved in obtaining a pure preparation of this protein. However, it has been possible to induce similar proteins in domestic animals which have been given a specific feed (SE Patent No. 9000028-2). Pigs given this feed obtained high levels of AF-like proteins and had a significant increase in the daily growth rate compared to matched controls. AF in rats challenged with toxin A from *C. difficile* protects not only against intestinal secretion but also against inflammation and bleeding in the gut.

A major object of the present invention is to provide a new recombinant protein and homologues and fragments (peptides) thereof for use in normalizing pathological fluid transport. These proteins and peptides are collectively called antisecretory factors (AF). The use of AF also partly inhibits, or totally eliminates the development of inflammatory reactions of various aetiologies. Reconstitution back to normal (fluid transport or inflammation) is obtained by the use of proteins or peptides. Further the AF proteins or peptides are effectively absorbed via various mucus membranes without losing in potency (when compared to intravenous administration). Consequently, a multitude of treatment regimens exist, and a correctly administered protein or peptide make it possible to rapidly reconstitute a deranged fluid (water and ion) balance, an inflammatory reaction, or both.

In summary, the recombinant AF (rAF) and the homologues and fragments thereof could be used for immunodetection, as feed additive for growing animals and as antidiarrheal and drugs against diseases involving edema, dehydration and/or inflammation.

The objects of the present invention are the following:

A recombinant protein having essentially the amino acid sequence shown in SEQ ID No. 2, or homologues or fragments thereof.

A fragment of the recombinant protein shown in SEQ ID No. 2, which fragment is chosen from the group comprising
  a) amino acids nos. 35–42
  b) amino acids nos. 35–46
  c) amino acids nos. 36–51
  d) amino acids nos. 36–80
  e) amino acids nos. 1–80
of the amino acid sequence shown in SEQ ID No. 2.

A peptide $X_1VCX_2X_3KX_4R$ corresponding to the fragment comprising the amino acids no. 35–42 of the recombinant protein shown in SEQ ID No. 2, wherein X is I or none, $X_2$ is H, R or K, $X_3$ is S, L or another neutral amino acid and $X_4$ is T or A.

Antibodies against a recombinant protein having essentially the amino acid sequence shown in SEQ ID No. 2, or homologues or fragments thereof.

A protein binding to antibodies specific to a recombinant protein having essentially the amino acid sequence shown in SEQ ID No. 2, or homologues or fragments thereof.

A composition for normalising pathological fluid transport and/or inflammatory reactions comprising as an active principal an effective amount of the recombinant protein having essentially the amino acid sequence shown in SEQ ID No. 2, or homologues or fragments thereof.

Use of a recombinant protein having essentially the amino acid sequence shown in SEQ ID No. 2, or homologues or fragments thereof for manufacturing a composition for normalising pathological fluid transport and/or inflammatory reactions.

Feed for normalising pathological fluid transport and/or inflammatory reactions in vertebrates, comprising as an active agent a recombinant protein having essentially the amino acid sequence shown in SEQ ID No. 2, or homologues or fragments thereof, or an organism capable of producing such a protein or homologues or fragments thereof.

A process of normalising pathological fluid transport and/or inflammatory reactions in vertebrates, comprising administering to the vertebrate an effective amount of a recombinant protein having essentially the amino acid sequence shown in SEQ ID No. 2, or homologues or fragments thereof, or an organism producing said protein or homologues or fragments.

Use of specific antibodies against a recombinant protein having essentially the amino acid sequence shown in SEQ ID No. 2, or homologues or fragments thereof, for detecting said protein or fragments in organisms.

Nucleic acids coding for a recombinant protein having essentially the sequence shown in SEQ ID NO. 1, or homologues or fragments thereof.

Use of nucleic acids coding for a recombinant protein having essentially the amino acid sequence shown in SEQ ID No. 2, or homologues or fragments thereof, for producing corresponding proteins or homologues or fragments.

Use of probes or primers derived from nucleic acids coding for a recombinant protein having essentially the sequence shown in SEQ. ID No. 2, or homologues or fragments thereof, for detecting the presence of nucleic acids in organisms.

Vector comprising nucleic acids coding for a recombinant protein having essentially the amino acid sequence shown in SEQ. ID NO. 2, or homologues or fragments thereof.

Host except human comprising a vector including nucleic acids coding for a recombinant protein having essentially the amino acid sequence shown in SEQ. ID No. 1, or homologues or fragments thereof.

A strain of an organism except human capable of producing a protein having essentially the amino acid sequence shown in SEQ ID No. 2, or homologues or fragments thereof.

As organisms capable of producing the recombinant protein use can be made of different types of organisms, such as recombinant bacteria and eucaryotic organisms, such as yeast, plants and vertebrates except humans.

Despite ten years of attempts to purify AF by conventional biochemical techniques, it has not been possible to obtain AF in a homogeneous form. However, by means of a new procedure of preparing a semipure AF for immunisation and selecting antiserum by means of an immunohistochemical method a suitable antiserum was chosen. With this antiserum it has now been possible to clone recombinant human cDNA expressing AF in *E. coli.*

The sequence of the new cDNA was determined and shown to be unique. By knowledge of this sequence, oligonucleotide probes were constructed which hybridise with human and porcine pituitary RNA. The size of this RNA, about 1400 basepairs, complies with the size of the sequenced cDNA comprising 1309 basepairs plus a poly(A) tail. A partial cDNA sequence from rat pituitary gland has been shown to be identical with that of the human cDNA reflecting a ubiquitous structure conserved in AF genes from different species. This resemblance makes it possible to use the same oligonucleotide probes to identify AF-coding RNA and DNA from different species.

It has furthermore been possible to express the rAF in a biological active form. The AF protein in form of a fusion protein with glutathione S-transferase was expressed in large amounts in *E. coli* and purified to homogeneity by affinity chromatography. After cleavage of the fusion protein with thrombin, the recombinant AF (rAF) was shown to be extremely potent, 44 ng ($10^{-12}$ mol) giving a half-maximal inhibition of cholera toxin-induced fluid secretion in rat intestine.

By gene technique smaller fragments of rAF was produced. The activity was shown to reside in a small sequence consisting of 7 to 8 amino acids. This was confirmed by help of chemical solid phase synthesis by which technique an octapeptide was produced and shown to be almost as biological potent as rAF on molar basis. With help of site directed synthesis a variety of sequences within the active site was constructed and replacements of certain amino acids shown to be possible without abolishing the biological activity.

The fluid secretion was measured by the intestinal loop model: a section (loop) of the small intestine is ligated by means of two satures; in the loop a certain amount of enterotoxin is injected. If antisecretory drugs are tested they are injected between one hour before and two hours after toxin challenge. The injection was made by three different routes; intravenously, intraintestinally and intranasally. The fluid is accumulating in the loop 5 h after toxin challenge. The secretion is calculated from the weight of the accumulated fluid per cm intestine.

The sequence of the protein was determined both directly by amino acid sequencing and indirectly by deduction from the cDNA sequence.

Recombinant AF seems to exert very little toxic or systemic effects since no obvious toxic reactions were noted in rats given 100 fold higher doses than that causing half-maximal inhibition. Since it is efficient when injected in the small intestine it could be administrated perorally.

The recombinant AF inhibits secretion also when injected after toxin challenge in contrast to the preparations of natural AF tested which seem to efficient only when injected before the toxin. Thus, rAF could be used both prophylactically and therapeutically.

Further, rAF and its peptide fragments were shown to inhibit cytotoxic reactions and inflammation in the gut caused by toxin A from *Clostridium difficile*. By help of a dye permeability test rAF and its fragements were shown to reverse pathological permeability changes induced by cholera toxin not only in the intestinal mucusa but also in plexus choroideus which regulates the fluid pressure in the brain.

Antisera against rAF were produced in rabbits and used in enzyme-linked immuno assays (ELISA). This assay might be used to measure AF in body fluids or feed.

A method of purifying antibodies against AF (natural or recombinant) by means of affinity chromatography on columns with agarose coupled rAF is reported below.

The antibodies were also shown to be efficient for detection of AF in tissue sections by means of immunohistochemical techniques and for detection of AF in Western-blot.

The invention will now be described further by means of the following non-limiting Examples together with the accompanying drawings.

EXAMPLE 1
Antibodies Against AF Produced for Cloning of cDNA

Antisecretory factor was prepared from pig blood by means of affinity chromatography on agarose and isoelectric focusing. To one liter of pig blood (containing anticoagulating substances) 1 g of sodium thiosulfate and 1 mg of phenylmethylsulfonylfluoride were added. The blood cells were separated by centrifugation and the clear plasma was eluted through a column with Sepharose 6B (Pharmacia LKB Biotechnology Stockholm), the gel volume corresponding to about 10% of the volume of the solution. After washing with three bed volumes of phosphate buffered saline (PBS=0.15 M NaCl, 0.05 M sodium phosphate, pH 7.2), the column was eluted with two bed volumes of 1 M α-methyl-D-glucoside dissolved in PBS. The eluate was concentrated and dialysed against water on an "Omega 10k flow through" ultrafilter (Filtron Technology Corp.). The fraction was subsequently fractionated by isoelectric focusing in an ampholine (Pharmacia) gradient pH 4–6 on a 400 ml isoelectrofocusing column (LKB, Sweden). A fraction having an isoelectric point between 4.7 and 4.9 was collected and dialysed against PBS. Thus, partially purified AF was divided into small aliquotes and used for production of antiserum in rabbits according to a previously described method.

The rabbits were immunised and the sera tested for their capacity to stain intracellular material in sections of human pituitary gland (method described in Example 6). Only one of the sera showed specific and distinct intracellular staining without staining extracellular matrix proteins. This antiserum was selected for screening of a cDNA/lambda phage GT11 library from human pituitary gland expressing proteins in E. coli.

EXAMPLE 2
Screening cDNA Libraries from Human Pituitary Gland and Brain

A 5'-stretch cDNA library from normal human pituitary gland, derived from tissues obtained from a pool of nine caucasians, was purchased from Clontech Laboratories. For screening of the library, phages were plated at $3 \times 10^4$ plaque forming units per 150 mm dish on E. coli Y1090. The previously described rabbit antiserum against porcine AF was absorbed with 0.5 volumes of E. coli Y1090-lysate for 4 hours at 23° C. and diluted to a ratio of 1:400 and screening performed according to Young and Davis (1). Alkaline-phosphatase-conjugated goat anti-rabbit antibodies were used as second antibodies (Jackson). Positive plaques were picked, eluted into phage suspension medium [20 mM Tris-HCl (pH 7.5), 100 mM NaCl, 10 mM $MgSO_4$, 2% gelatin], replated, and screened until all plaques tested were positive.

cDNA-recloning—Phage DNA from AF recombinants was isolated with Wizard Lambda Preps (Promega) and digested with EcoR1. The inserts were purified with Sephaglas BandPrep Kits (Pharmacia), recloned into pGex-1λT vector (Pharmacia) as described by the manufacturer and transfected into Epicurian Coli XL1-Blue, Top 1 cells or BL21 cells (all three from Stratagen). rAF or rpeptides were prepared in BL21 cells when not stated otherwise (2).

Amplification of cDNA by PCR—To obtain the missing 5'-end of the cDNA a PCR-based method called RACE (rapid amplification of cDNA ends) was performed. A modified RACE-method that generates 5'-RACE-Ready cDNA with an anchor oligonucleotide ligated to the 3'-ends of the human brain cDNA molecules was purchased from Clontech Laboratories. The 5'-end was amplified from a portion of the 5'-RACE-Ready cDNA in two PCR amplification steps using a 5' primer complementary to the anchor and two nested gene-specific 3' PCR primers A and B (A=base 429–411 and B=base 376–359; FIG. 1a). Various smaller portions of the RACE fragment was further amplified in order to express the corresponding peptides and test for their biological properties. The position of the base and amino acid at the start and end of these oligonucleotide fragments and their corresponding peptides are shown in Table 1. Porcine and bovine cDNA (Clontech Laboratories) was used as templet for amplifying fragments corresponding to N3 in Table 1. Variation of the sequence was also inserted artificially by site directed mutagenesis in which method various oligonucleotides corresponding to position 168–193 was synthesised in order to replace one by one of amino acid 35–42 (positions as shown in SEQ ID NO. 2). The amplified DNA fragment was cloned into pGex-1λT vector by using the EcoR1 site built into the anchor and the gene-specific primer. To verify the sequence obtained by the RACE method, double stranded cDNA from human pituitary gland and brain (Clontech) were amplified with primer pair C/D containing an extra EcoR1-cleavage site (FIG. 1b). The primers were designed to allow the entire open reading frame (ORF) to be amplified. The pituitary and brain PCR-products of expected size were digested with EcoR1, isolated and cloned into the plasmid pGex-1λT vector.

DNA sequencing and oligonucleotides—DNA from plasmid pGex-1λT was used as a template for sequencing of the inserts by dideoxy-chain-termination method (15) using the Sequenase version 2.0 kit (U.S. Biochemical Corp.). Initial forward and reverse primers copying regions of pGex-1λT immediately upstream and downstream of inserted DNA were obtained from Pharmacia. Subsequent primers were synthesised (Scandinavian Gene Synthesis AB) on the basis of sequence information obtained. Three different PCR clones were sequenced in order to avoid base-exchange by Taq polymerase in the 5'-RACE method.

Nucleotide sequence and the deduced protein sequence data were compiled and analysed by using MacVector 4.1 (Eastman Chemical Co.). To predict the corresponding amino acid sequence of the cDNA inserts, codon usage of different reading frames was compared and gave one large open reading frame. Interrogation of DNA and protein sequence data was carried out by use of an Entrez CD-ROM disc (National Center for Biotechnology Information, Bethesda, USA).

Molecular cloning and sequence analysis of cDNA—Polyvalent antisera against AF protein from pig were used for screening cDNA from human pituitary glands. Two clones expressing immunoreactive AF were isolated, rescued from phage lambda and recloned into the EcoR1 site of vector pGex-1λT as described in the kit provided from Pharmacia. Restriction analysis gave insert sizes of 1100 and 900 bp, respectively. DNA-sequencing of the two clones revealed homology to be complete except for one substitution (FIG. 1, C replacing T at position 1011). A sequence upstream of the 5'-end of clone 2 was obtained by means of the RACE method. The fragment had a total length of 376 bp (not including the synthetic nucleotide arm at the 5'-end). The total reconstructed cDNA contained 1309 basepairs followed a poly-A tail, which was preceded by a poly-A signal (FIG. 1, positions 1289–1295). An open reading frame (ORF) of 1146 bp (positions 63–1208) was identified.

EXAMPLE 3
Expression of Mammalian AF Protein from Recombinant Plasmids

Construction and purification of fusion proteins—The cDNA-clones obtained by immunological screening and by PCR amplification of the entire cDNA were ligated to pGex-1λT. This vector allows expression of foreign proteins in *E.coli* as fusions to the C terminus of the *Schistosoma japonicum* 26 kDa glutathione S-transferase (GST), which can be affinity purified under nondenaturing conditions with help of the kit provided from Pharmacia. Briefly, overnight cultures of *E.coli* transformed with recombinant pGex-1λT plasmids were diluted in fresh medium and grown for a further 3 h at 37° C. Protein expression was induced by 0.1 mM IPTG (isopropyl-beta-D-thiogalactopyranoside), and after a further 4 h of growth at 30° C., the cells were pelleted and resuspended in PBS. Cells were lyzed by sonication, treated with 1% Triton X-100 and centrifuged at 12000×g for 10 min; the supernatant containing the expressed fusion proteins was purified by passing the lysates through glutathione agarose (Pharmacia). The fusion proteins were either eluted by competition with free glutathione or were cleaved overnight with 10 U bovine thrombin to remove the AF-protein from the GST affinity tail. The entire method of using the pGex plasmid and purifying the recombinant proteins or peptides was performed by means of the kits provided from Pharmacia.

Sequence and size of recombinant AF-proteins—To confirm the coding sequence, the full-length transcript was isolated by using PCR-amplification of pituitary and brain cDNA. Using the primer pair C/D, 1215 bp identical to the sequence of clone-4 (FIG. 1, SEQ ID NO:1) was isolated. The open-reading frame encoded 382 amino acids with a calculated molecular mass of 41.14 kDa and a calculated pI of 4.9.

The AF clones-1, 2 and 3 as well as the oligonucleotides N1–N5 (FIG. 1 and Table 1) were ligated into the pGEX-1λT plasmid vector so that the ORF was in frame with the glutathione S-transferase (GST) protein. The constructs were transformed into *E.coli*, and expression of fusion proteins was induced with IPTG. The purified fusion proteins and the thrombin-cleaved AF protein or peptide were subjected to SDS-PAGE and Western blotting using antiserum against porcine antisecretory factor (FIG. 2). Coomassie brilliant blue staining of the proteins revealed discrete bands for each protein except for the GST-AF-1 protein which manifested degradation into smaller components.

Solid phase peptide synthesis—Smaller peptides ($P_7$ to $P_{18}$ in Table 1) was produced (K. J. Ross-Petersen AS) on solid phase in an Applied Biosystems peptide synthesiser. The purity of each peptide was 93–100% as evaluated on reversed phase HPLC on Deltapak C18, 300 A using a linear gradient of 0.1% trifluoro acetic acid in water/acetonitril.

Amino acid sequencing—Protein sequence analysis was performed to further validate the identified ORF. The pure AF proteins were run in 10% macro-slab gel SDS-PAGE (14) and the proteins transferred to a Problot membrane (Applied Biosystems) by electroblotting (Bio-Rad). Spots, visualised by Ponceau S staining, were excised from the blot and the first 20 amino acids of the proteins were sequenced by automated Edman degradation on an automatic sequencer (Applied Biosystems).

The N-terminal sequences of clone-2 and clone-3 were determined, and shown to perfectly match amino acids 63–75 and 130–140, respectively, of the predicted sequence (FIG. 1, SEQ ID NO: 1).

Comparison with other protein sequences available from GenBank revealed that the sequence of rAF (FIG. 1, SEQ ID NO:1) is unique in all its parts and no similar sequence has been reported.

The first ten residues of the protein appear to be relatively hydrophobic when analysed according to Kyte-Doolittle (22) and might constitute a signal peptide, which is cleaved out prior to exocytosis of the protein. This interpretation is supported by the Western blot analyses (FIG. 3) in which the recombinant protein appeared to have a slightly higher molecular mass than the protein extract from pituitary gland. Some of this difference, however, might also be due to the additional five amino acids in the recombinant protein constituting the thrombin cleavage site of the fusion protein.

EXAMPLE 4

Production and Testing Antisera Against rAF

Antisera against recombinant GST-AF fusion protein—Antibodies against the purified fusion proteins GST-AF-1, GST-AF-2 and thrombin-cleaved pure AF-1 protein (=rAF) for use in ELISA, Western blot and immunohistochemical studies were produced in rabbits. Each rabbit was given 100 μg of antigen in 1 ml PBS mixed with an equal volume of Freund's complete adjuvant; each immunisation was distributed in 8–10 portions injected in the back intracutaneously. Two booster doses with 50 μg antigen were injected at 3 and 5 weeks, the last one without Freund's complete adjuvant. The rabbits were bled 6 days after last booster and sera were prepared and stored at −20° C. The sensitivity of the antiserum was tested with a dot blot assay. GST-AF-2 was applied on an ECL nitrocellulose membrane in 1/5 dilutions, and the antiserum diluted 1:1000. The membrane was blocked with 1% bovine serum albumin (BSA) in PBS at 4° C. for 16 h, and then incubated for 1½ h with a 1:800 dilution of rabbit anti-GST-AF or porcine AF antiserum. The blot was developed with alkaline phosphatase-conjugated goat anti-rabbit immunoglobulin followed by 5-bromo-4-chloro-3-indolyl phosphate and p-nitro blue tetrazolium (Boehringer Mannheim). The estimated limit for antigen detection was about 1 ng in this test.

SDS-polyacrylamide gel electrophoresis and immunoblotting—SDS-polyacrylamide gel electrophoresis (SDS-PAGE) of human and porcine pituitary gland extracts and pure AF-proteins was performed in 10% acrylamide minislab gels, essentially as described by Laemmli (4) with the modification that bis-acrylamide as a cross-linker was replaced by N,N'-diallyltartardiamide with the corresponding molarity. Pyronin Y (Sigma) was used as a marker of the electrophoretic front. Prestained molecular weight reference were purchased from BDH. Proteins were then either stained with Coomassie brilliant blue or transferred electrophoretically to 0.45 mm pore-size ECL nitro-cellulose (Amersham) for immunoblotting. The subsequent incubations with BSA, conjugated anti-IgG and alkaline phosphatase substrate were the same as for the dot blot assay described above.

As stated above Coomassie Brilliant Blue staining revealed no discrete band for the GST-AF-1 protein, which was probably due to proteolytic degradation into smaller components. However, in the Western blot analyses the full length protein gave a much stronger signal than the degradated products (FIG. 2b). The strong reaction with the antiserum against porcine AF indicated that the recombinant proteins indeed have the same immunoreactivity as AF. The molecular weight of the full length protein appeared to be about 60 kDa which is higher than the true mol. wt of 41139 Da estimated from the amino acid composition. Furthermore, the proteins were also immunoblotted and probed with antiserum raised against GST-AF-2, which bound to the thrombin-cleaved proteins (FIG. 3).

Figure 3A:
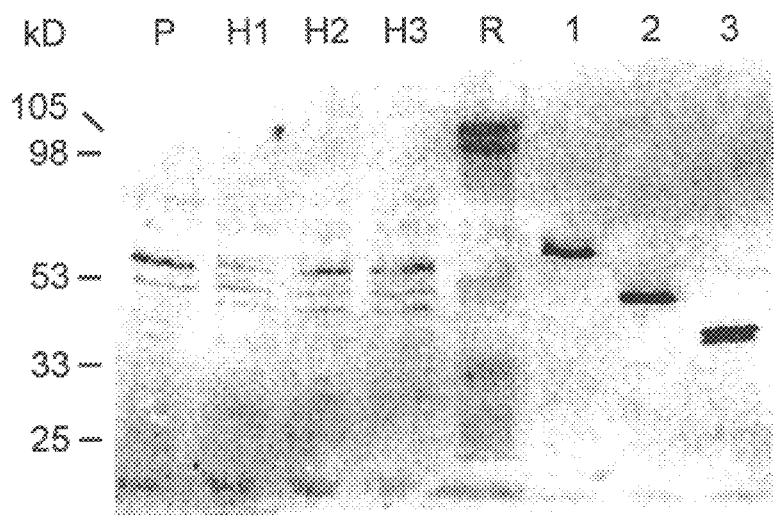

Antiserum against recombinant GST-AF-2 reacted with the naturally occurring AF protein of an apparent mol mass of 60 kDa, and with some smaller components, probably enzymatic degradation products (FIG. 3a).

Figure 3B:
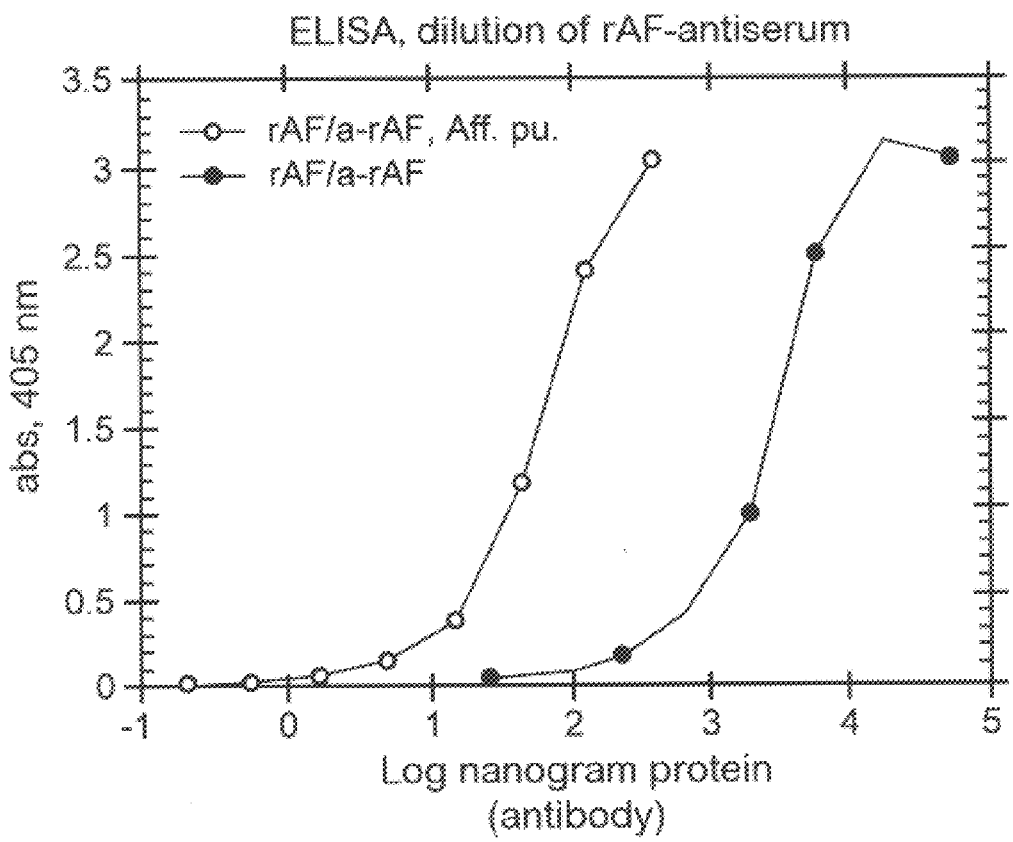
Figure 5A:
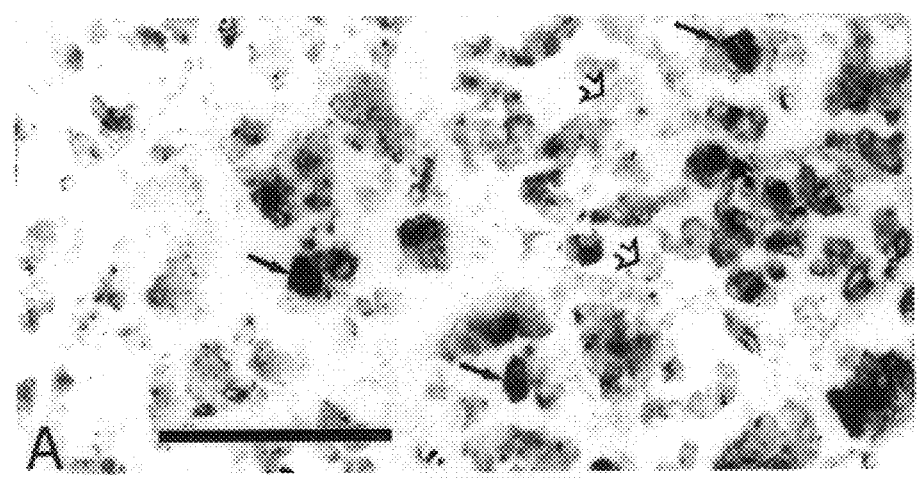
Figure 5B:
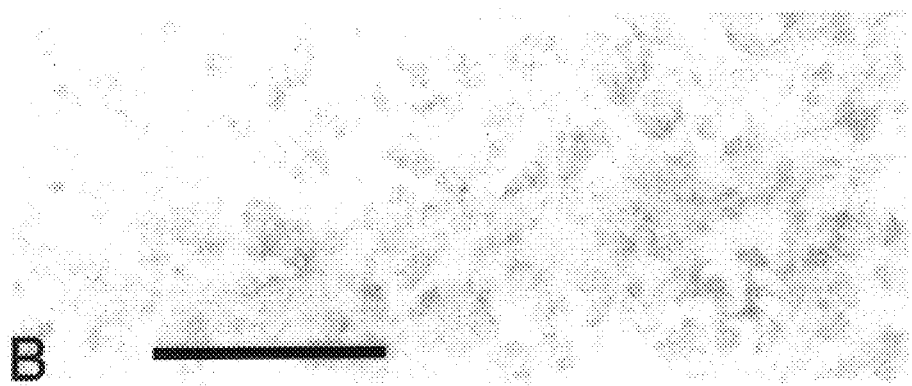
Figure 5C:
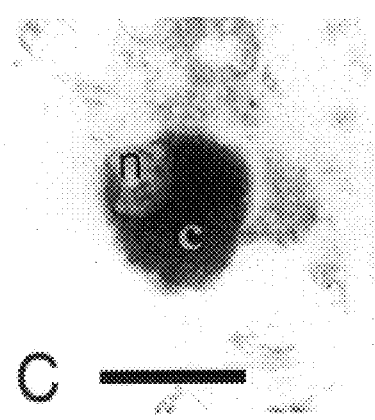
Figure 5D:
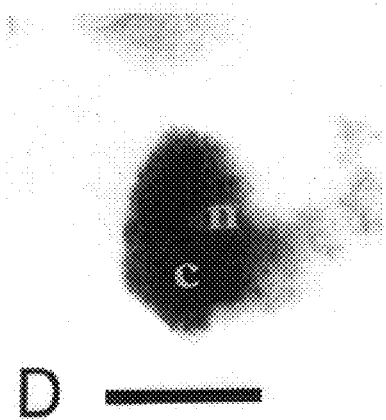

ELISA for determination of AF-concentrations—ELISA assays were performed using anti-AF-1 and anti-AF-2 according to a previously described method (5). As shown in FIG. 3b the sensitivity of the test with the crude antiserum was between 1–10 μg protein whereas the test with the affinity purified antibody had a sensitivity between 5 and 50 ng protein.

EXAMPLE 5
Northern Blot Analysis of RNA from Pituitary Gland

Northern blot analysis—Human pituitary glands were obtained postmortem from Sahlgrenska Hospital (permission given by Swedish Health and Welfare Board; 2§ transplantationslagen, 1975:190). To obtain RNA, pituitary glands were extracted with guanidinium thiocyanate RNA according to Chomczynski and Sacchi (6). Polyadenylated RNA was selected by means of a commercial kit (Pharmacia) using columns with oligodT-cellulose. In addition, a pool of human pituitary mRNA from 107 individuals purchased from Clontech was used. Five μg of each sample of poly(A+)RNA was glyoxal-treated and electrophoresed in a 1.2% agarose gel (7). After capillary alkaline transfer for 3 h in 0.05 M NaOH to Hybond N+ nylon membranes (Amersham), prehybridisation and hybridisation were carried out for 24 h each at 42° C. The hybridisation solution contained 50% formamide, 5×SSPE, 10×Denhard's solution with 250 μg/ml denaturated low-MW DNA and 50 μg/ml polyadenylic acid. The blots were probed with four different antisense 28 bp oligonucleotides comprising the positions 132–105 (primer E), 297–270 (primer F), 748–721 (primer G) and 833–806 (primer H) of the sequence (FIG. 1); the probes were 3'-end labelled with terminal transferase (Boehringer Mannheim) plus [$\alpha^{32P}$]ddATP (Amersham) and purified on Nick columns (Pharmacia). Five postwashes in 5×SSPE/0.1% SDS—0.5×SSPE/0.1% SDS were made at 42° C. for 30 min each time, with a repeat of the last wash. Filters were exposed to Hyperfilm MP (Amersham) for 7 days.

Expression in pituitary gland—Northern blot analyses were performed with a mixture of four oligonucleotide probes hybridising with different sequences along the cloned cDNA (FIG. 4). The probes hybridised with a single band of about 1400 bp in the separated mRNA from pituitary gland. The strongest signals were obtained with the human material, but the porcine material also cross-reacted.

EXAMPLE 6
Distribution of AF in Sections of Pituitary Gland

Species and tissues—Human pituitary glands were obtained postmortem from Sahlgrenska Hospital (permission given by the Swedish Health and Welfare Board; §2 transplantationslagen, 1975:190). Glands were kept frozen at −70° C., except those used for histological examination which were fixed for 24 h in 4% paraformaldehyde dissolved in phosphate-buffered saline (PBS=0.15 M NaCl, 0.05 M sodium phosphate, pH 7.2) and thereafter transferred to 7.5% sucrose in PBS. Pituitary glands from pigs, 5–7 months old, obtained from a slaughter house, were placed on dry ice during transport and kept frozen at −70° C. until used. Sprague-Dawley rats, 2–3 months old, were obtained for bioassay from B & K Universal AB, Sollentuna, Sweden. Rabbits (New Zealand White) for immunisations were obtained from Lidköping Kaninfarm, Sweden.

Immunohistochemistry—The fixed pituitary glands were frozen in liquid nitrogen, and cryo sections, 7 μm thick, were prepared. From each sample 5–10 sections comprising different parts of the gland were fastened to microscope slides. The sections were blocked in 5% fat-free dried milk and incubated with primary rabbit antiserum (anti-GST-AF-2 fusion protein) diluted 1:4000–1:8000 in a humid chamber overnight at 4° C. After rinsing in buffer, the specimens were incubated for 1 h at 23° C. with alkaline phosphatase-conjugated swine anti-rabbit immunoglobulins diluted 1:50 (Dako A/S). The immunoreaction was visualised with phosphatase substrates as described elsewhere (8). Control sections were incubated with immune serum absorbed with an excess of GST-AF-2 protein or with all incubation steps except the primary antibody.

Distribution of AF in sections of pituitary gland. The distribution of AF in sections of human pituitary glands was studied with immunohistochemical techniques (FIG. 5). In all specimens investigated, a moderate number of cells in the adenohypophysis were stained; the immunostained material appeared to be located in granules in the cytoplasm; preabsorption of the immune serum with an excess of GST-AF-2 protein abolished the signal. No staining was observed in the posterior part (neurohypophysis).

The distribution of immunoreactive material in the pituitary gland demonstrated solely intracellular distribution of AF in secreting cells of the anterior lobe (adenophypophysis). The proteins emanating from this lobe include growth hormone, thyrotropin, corticotropin, prolactin and luteinising hormone. The passage of these hormones from intracellular localisation to the vascular system is triggered by releasing factors produced by neuroendocrinic cells in the hypothalamus.

EXAMPLE 7
Biological Activity of rAF

Antisecretory activity—The antisecretory activity was measured in a rat intestinal loop model previously described (9). A jejunal loop was challenged with 3 μg of cholera toxin. Either different doses of purified AF-1-proteins or PBS (control) was injected before or after the challenge with cholera toxin. The weight of the accumulated fluid in the intestinal loop (mg/cm) was recorded after five hours. Each AF preparation was tested in at least six rats. Fisher's PLSD was used for statistical analysis of the data.

Figure 6:
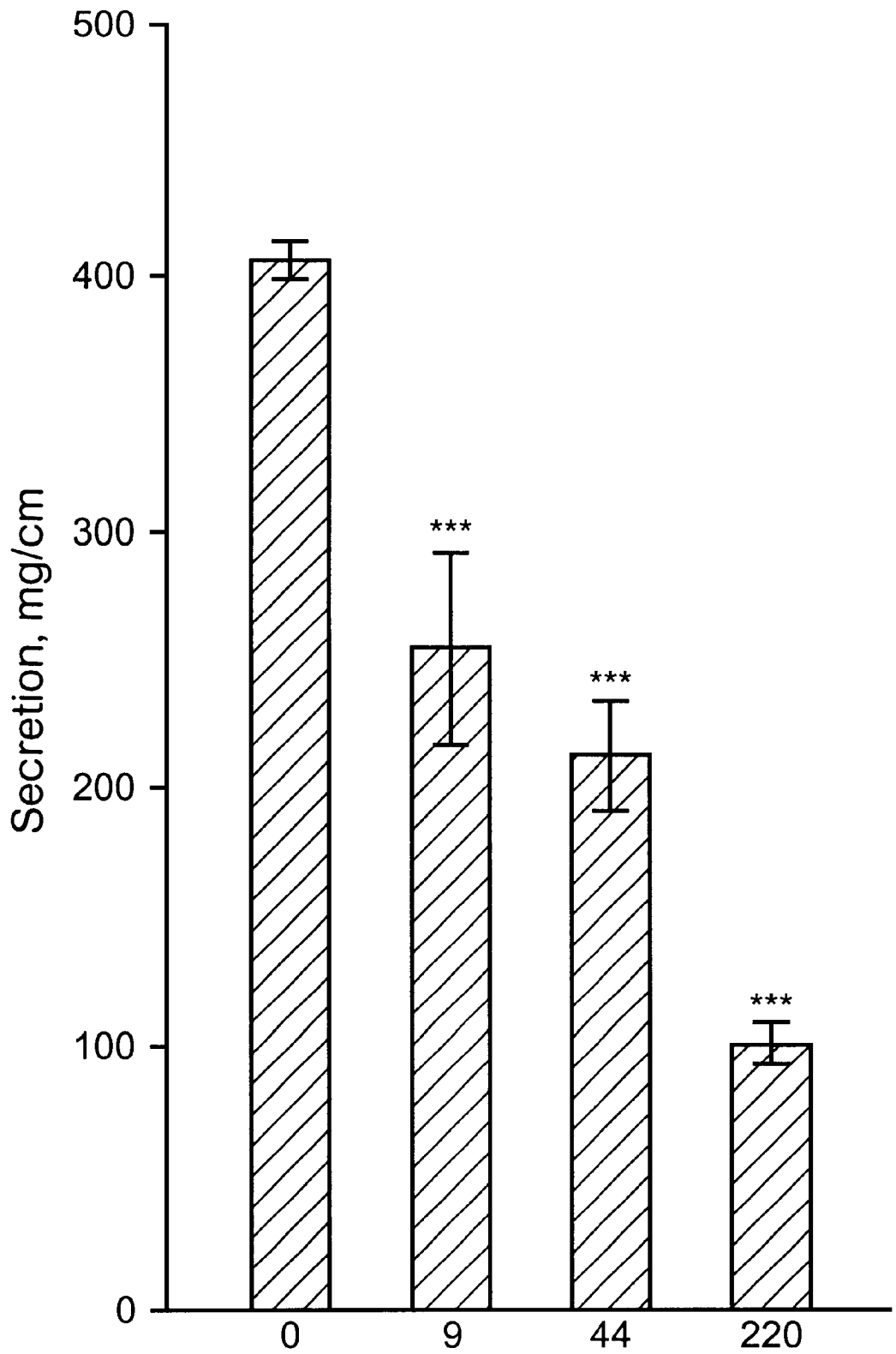

Biological activity of rAF protein—The biological activity of the pure rAF protein of clone-1 produced in $E.coli$ was tested in a rat model. The capacity of the rAF to inhibit intestinal fluid secretion when injected intravenously 20–30 sec before intestinal challenge with cholera toxin is shown in FIG. 6. In control animals injected with buffer only, the cholera toxin caused a pronounced secretion, 412±9 mg fluid per cm intestine. The pure rAF caused dose-dependent inhibition of the cholera secretion which was significantly different from the response to the buffer ($p<0.01$, $n=6$). Nine ng of clone-1 protein is sufficient to reduce the response by 34%, whereas 44 ng ($10^{-12}$ mol) and 220 ng reduced it by 46% and 78%, respectively. The biological activity of recombinant AF is greater than that of any enterotoxin known to us and greater than that of any intestinal hormone or neuropeptide modifying water and electrolyte transport. Moreover, the level of activity of human rAF in rat is surprisingly high which probably reflects a ubiquitous structure conserved in rAF molecules from different species. This hypothesis is supported by the cross-reactivity between human and porcine material obtained in the Western blot and Northern blot analyses.

Figure 7:
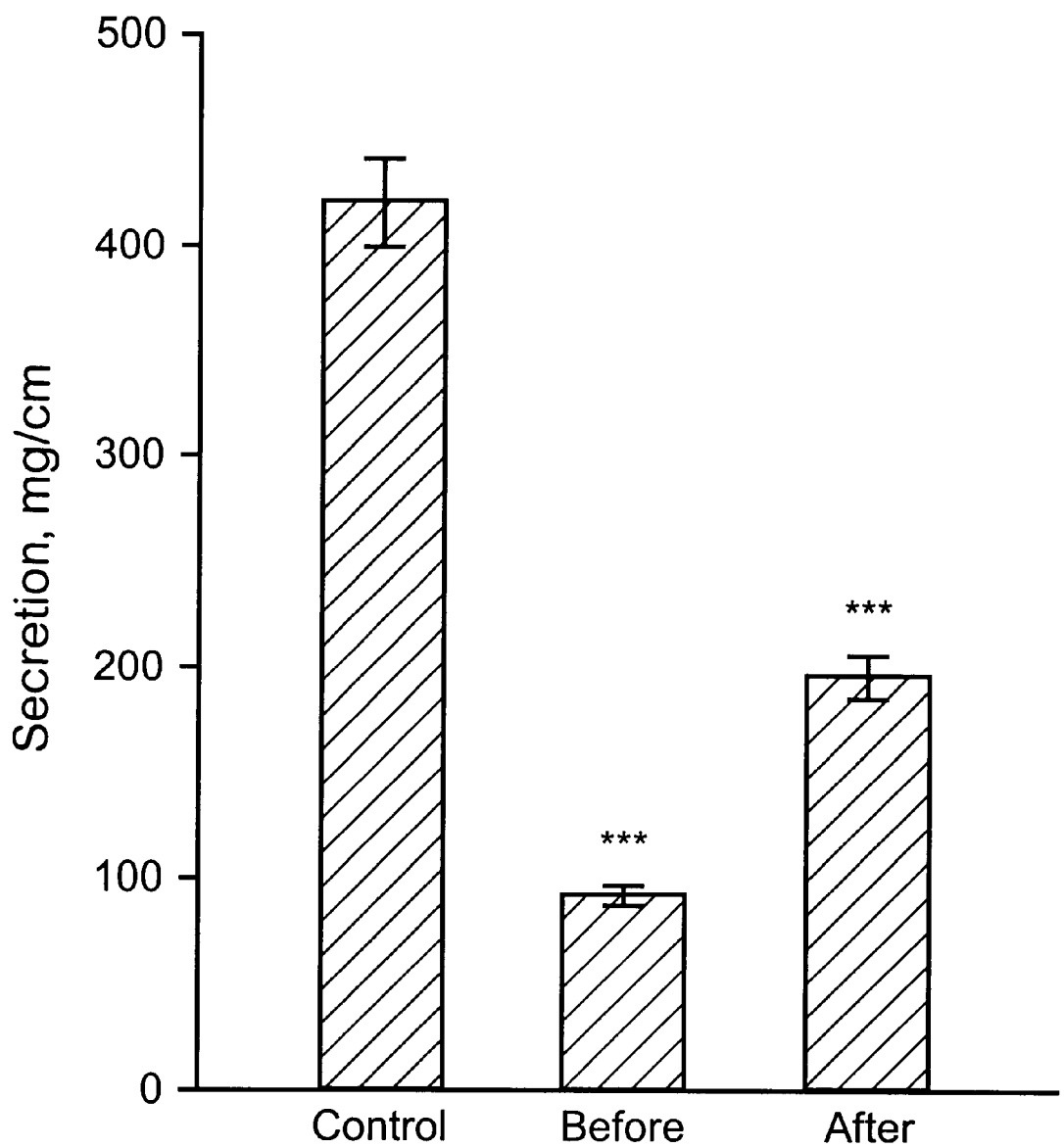

The capacity of 0.5 μg of rAF to inhibit intestinal secretion when injected intravenously 20–30 sec before and 90 min after cholera toxin challenge was compared (FIG. 7). Both administrations gave significant inhibition compared to control animals ($p<0.01$, $n=6$). Thus, in contrast to natural AF, the recombinant protein was also efficient when given after toxin challenge which make rAF useful for therapeutic treatment of diarrhea.

Figure 8:
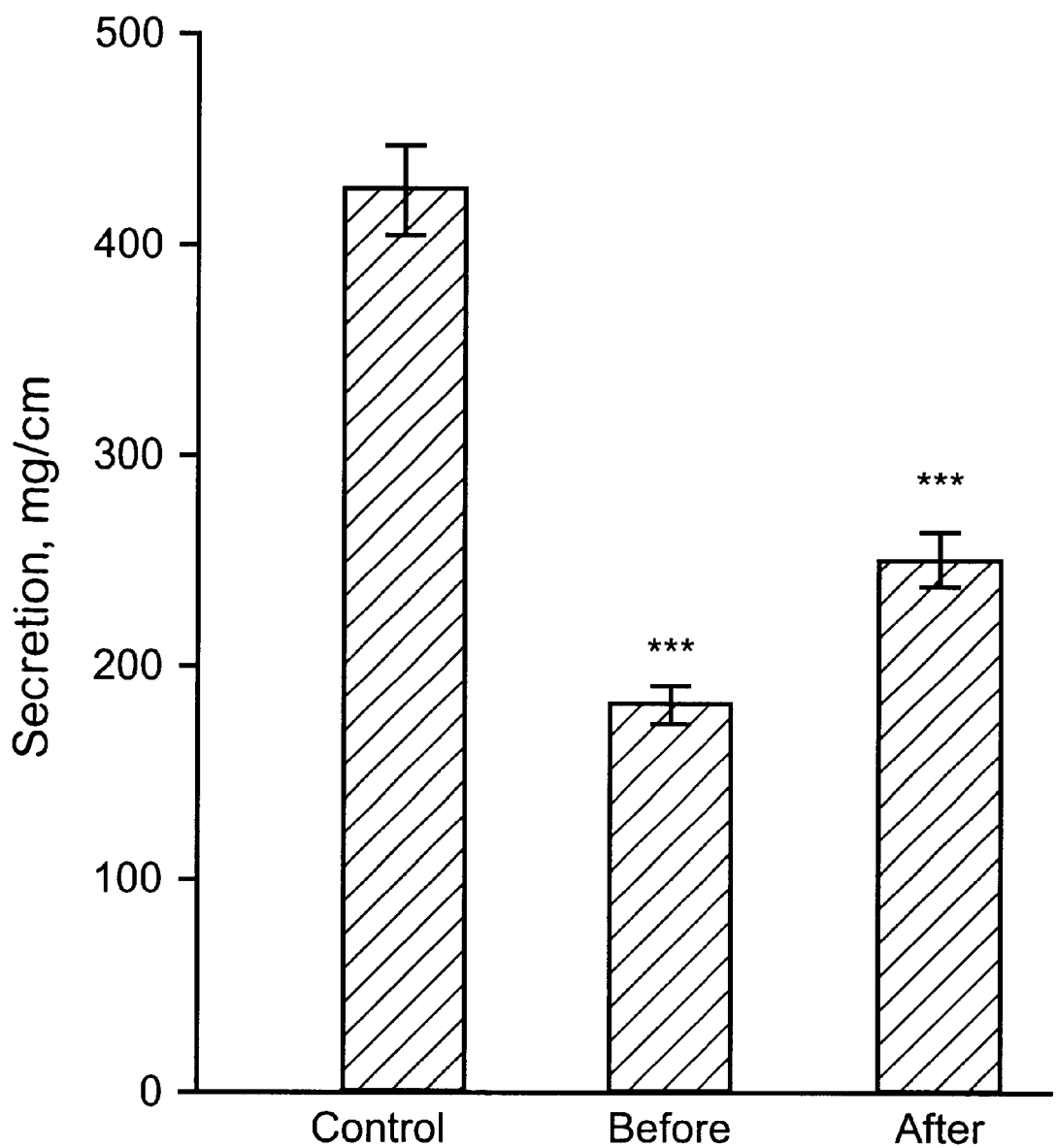
Figure 9A:
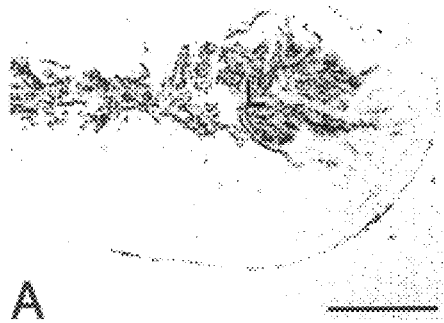
Figure 9B:
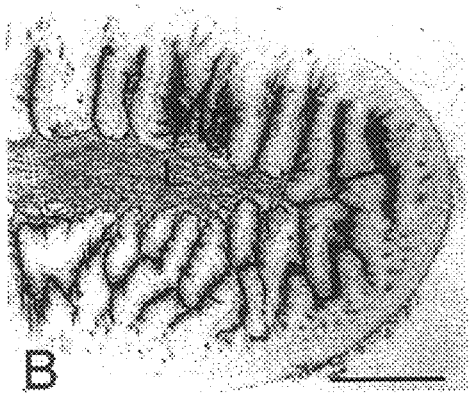
Figure 9C:
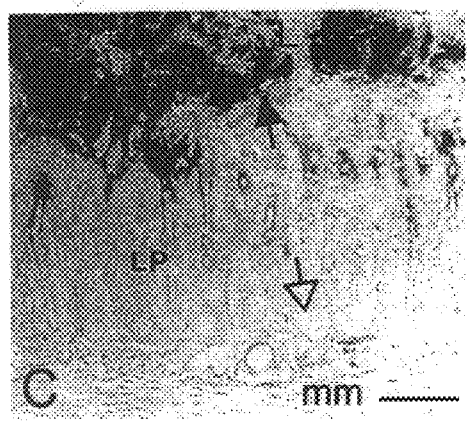
Figure 9D:
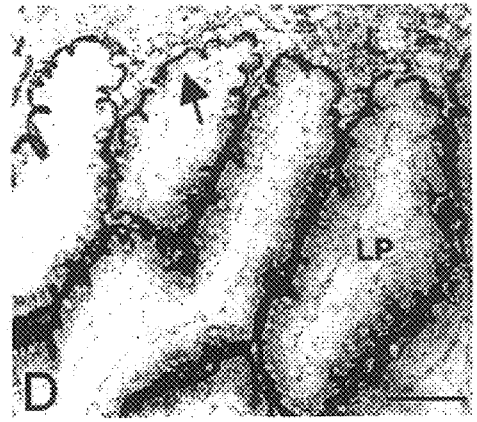
Figure 9E:
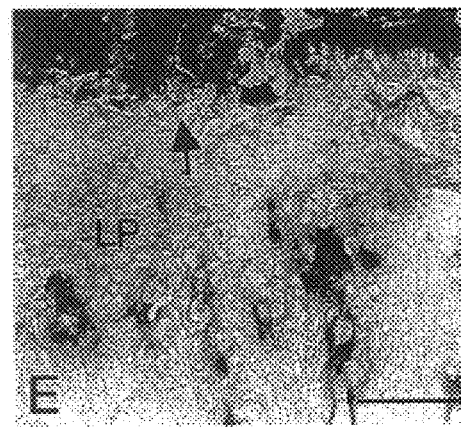
Figure 9F:
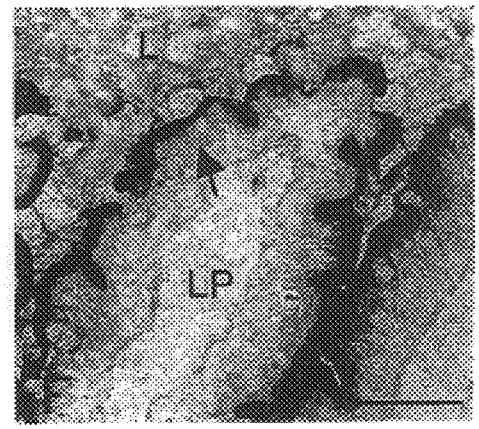

3 µg rAF was injected in a 8–10 cm long loop placed immediately proximal to the loop which was challenged with cholera toxin. The rAF was either induced 20–30 sec before or 90 min after the toxin-challenge. In FIG. 8 it is shown that both test groups obtained a significant reduction of the fluid secretion compared to controls (p<0.01, n=6); no difference was observed between the two test groups. This experiment suggests that rAF is active after oral administration and might be used as an additive in animal feed provided that no serious side effect is obtained.

In the Examples described above, the rAF was produced in *Epicurian Coli* XL-1 cells. In these cells much of the produced rAF was degraded into smaller peptides. When rAF was produced in BL21 cells only a small portion of the rAF was degraded while in Top 1 cells no degradation was observed. Surprisingly the biological activity was proportional to the extent of degradation, i.e. more degradation resulted in higher activity. Therefore various shorter fragments were produced in order to test for their possible biological activity.

As shown in Table 1, these fragments were tested intravenously prior to cholera toxin challenge in the same way as described above for the intact rAF. The peptides expressed by clone 2 and 3 tested in amounts of 0.1, 1 and 10 µg had no effect on the toxin response. In contrast one microgram of the peptide expressed by the RACE fragment (clone 4) had a pronounced effect. A lot of shorter constructs were made from the RACE fragment and expressed in pGex-1-lambda. As shown in Table 1, the active site was found to be situated between amino acid residue 35 to 51. In order to determine more exactly the active site three small peptides were made by solid phase peptide synthesis. Two of them were active, peptide 35–46 (P3) and peptide 35–42 (P1); the latter octapeptide IVCHSKTR (P1) was active in a dose less than 1 ng being almost as active in a molar basis as the intact rAF. In contrast a shorter hexapeptide VCHSKT (P2) exerted no effect when tested in doses between 1 ng and 10 μg.

A peptide $X_1VCX_2X_3KX_4R$ corresponding to the human fragment P1 but with certain changes and/or deletions, have also been produced by site directed mutagenesis and tested for biological activity. Comparison was also made of sequences from bovine and porcine cDNA. These studies suggested the following changes and/or deletions:

$X_1$ is I or none $X_2$ is H, R or K $X_3$ is S, L or another neutral amino acid $X_4$ is T or A.

TABLE 1

| Code | Oligonucleotide* | Peptide** | Inhibition of cholera secretion*** | pmol ED50 |
|---|---|---|---|---|
| N1 | 63–301 | 1–80 | + | 4 |
| N2 | 168–301 | 36–80 | + | 6 |
| N3 | 168–215 | 36–51 | + | 3 |
| N4 | 122–170 | 21–36 | – | |
| N5 | 186–269 | 42–69 | – | |
| P3 | S.P.S.**** | 35–46 | + | 7 |

TABLE 1-continued

| Code | Oligonucleotide* | Peptide** | Inhibition of cholera secretion*** | pmol ED50 |
|---|---|---|---|---|
| P1 | S.P.S. | 35–42 | + | 5 |
| P2 | S.P.S. | 36–41 | – | |

*Position of the basepair in SEQ ID NO:1 which was expressed in the construct made from the AF cDNA and pGex-1-lambda
**Positions of the amino acid-residues (SEQ ID NO:2) in AF at the start and end of the synthesised peptide.
***Inhibition of cholera toxin induced fluid secretion in a ligated rat intestinal loop; the amount (pmol) causing halfmaximal inhibition (ED50) is noted for active peptides.
****These peptides were produced by solid phase synthesis.

The effect of rAF on inflammation in the intestinal mucosa was also tested in the rat intestinal loop model. Thus, 20 rats were challenged with 0.5 μg of toxin A from *Clostridium difficile* (10) and the inflammatory and fluid secretion measured after 2.5 and 5 hours, respectively (10+10 rats). Half of the rats in each group received 100 ng of rAF intravenously 30 sec prior to the challenge; the other half received PBS buffer as control. After killing the rat, the loops was dissected out, and the middle 2–3 cm part of the loops were frozen on dry ice. The frozen specimens were then sectioned in 8 μm thick sections by use of a Leica cryostat. The sections were stained to demonstrate alkaline phosphatases by enzyme histochemistry. Alkaline phosphatases are expressed by the intestinal epithelial cells and the staining allows an assessment and of the integrity of the intestinal epithelium.

The results revealed (FIG. 9) that the control rats developed extensive damage of the intestinal mucosa: after 2.5 h shedding of epithelial cells from the basal membrane was observed together with necrotic tissue, whereas extensive bleeding was observed after 5 h. In contrast, animal treated with rAF developed no shedding, necrosis or bleeding. The toxin A-induced fluid secretion was also inhibited from 199±4 to 137±5 mg/cm after 2.5 h ($p<0.01$) and from 421±3 to 203±6 mg/cm after 6 h (5 rats/group, $p<0.01$).

A similar experiment was performed with 0.5 μg of the peptide IVCHSKTR (=P1) replacing the rAF protein. The octapeptide achieved the same effect on toxin A-induced intestinal inflammation and fluid secretion as shown in FIG. 9.

Toxicity—In order to test the toxicity of rAF it was injected in a high dose, 50 μg per rat. No obvious toxic reaction was registered during an observation period of one week.

EXAMPLE 8

Biological Activity of rAF on Intestinal Permeability

In order to evaluate the effect of rAF on the permeability of an organic substance dissolved in the blood a test with Evans blue dye was performed according to a previously described method (11). The experiment was initially performed as described above in Example 7 and FIG. 5 with intravenous injection of rAF prior to cholera toxin challenge. However, no fluid secretion was measured but 90 min after toxin challenge Evans blue dye, 1 ml of a 1.5% solution in PBS, was injected intravenously. The dye was allowed to circulate for a 5 min long period. Thereafter the rat was subjected to transcardial perfusion via the left ventricle—right atrium (using a peristaltic pump [Cole Parmer Instruments, Chicago, Ill., USA]) with 200 ml of 4° C. PBS/Alsevier's (1/1 ratio) solution during a period of some 150 sec, performed under ether anaesthesia. This procedure was undertaken in order to remove all of the EB present in the vascular system, leaving only the EB in the interstitial tissue to be detected by the formamide extraction of the dye.

The results in Table 2 demonstrate that CT-challenge significantly (p<0.001) increases the amount of EB that can be extracted from the intestinal tissue with some 43%, while an intravenous injection of 1 BrT prior to cholera toxin challenge prevent this increase, i.e. the amount of EB extracted from the tissue in group 1 (control) did not differ from that in group 3 (1 rAF+CT)

TABLE 2

| Group | Challenge | ng | EB/g int. tissue × $10^{-07}$ | % increase of EB-konc |
|-------|-----------|----|-------------------------------|-----------------------|
| 1 | PBS + PBS | 6 | 29.3 ± 1.0 | |
| 2 | PBS + CT | 6 | 51.8 ± 1.3 | 43 (p <0.001) |
| 3 | 1rAF + CT | 6 | 29.6 + 1.5 | 0 NS |

Figure 10A:
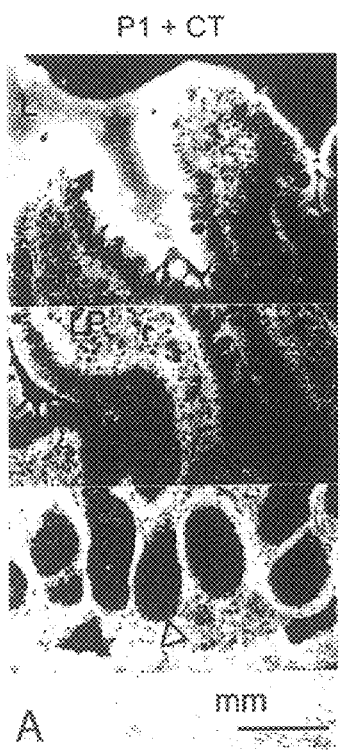
Figure 10B:
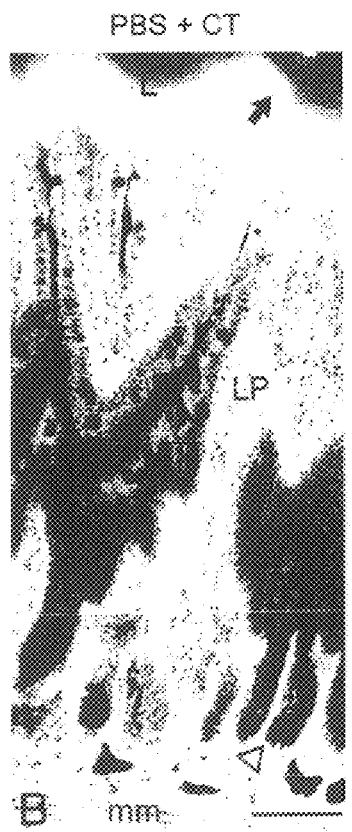
Figure 10C:
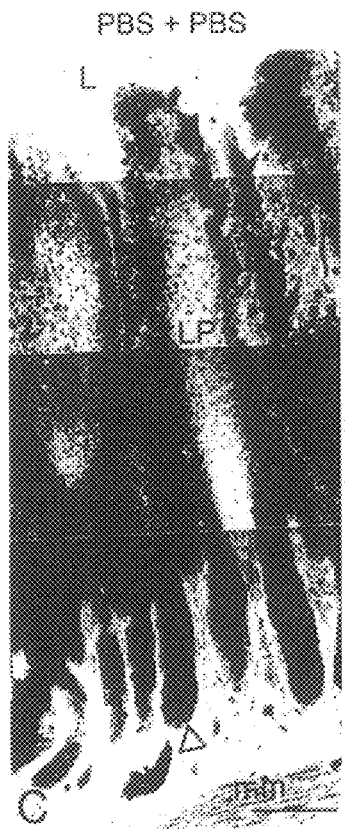
Figure 11A:
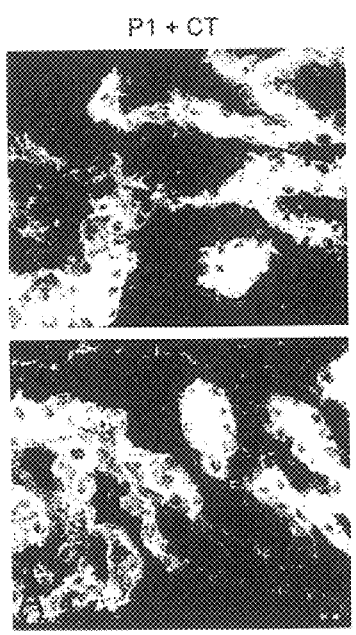
Figure 11B:
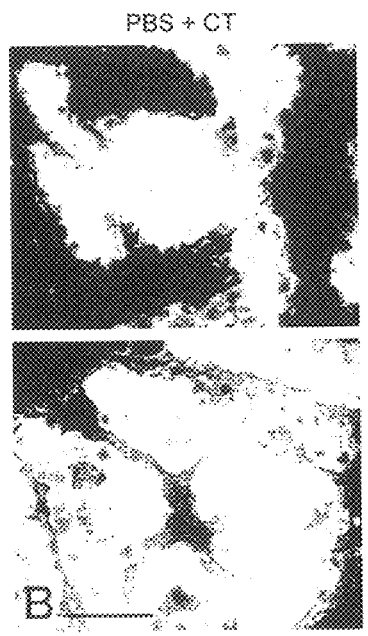
Figure 11C:
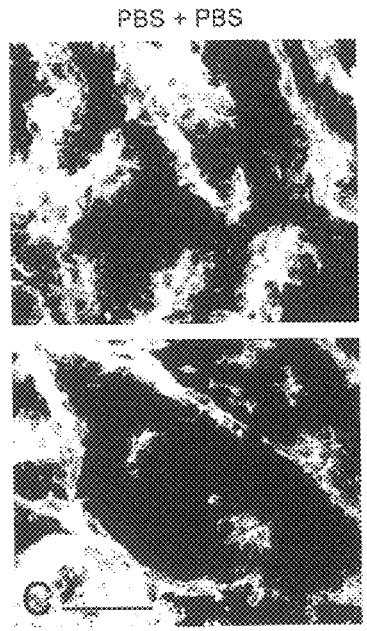

The results shown in FIGS. 10 and 11 demonstrate the extravasation of the azo dye Evans blue in the small intestine and in the corresponding plexus choroideus from the lateral ventricles of the brain after intestinal challenge with cholera toxin, with and without previous treatment of the rats with P1 (IVCHSKTR).

The experiments were performed in the following way: Male Sprague-Dawley rats, weighing 350 g, were starved for 18 h prior to the experimental procedure, but had free excess to water. The rats were used in groups of six. The peptide P1, cholera toxin (CT), and PBS were administrated according to Table 3.

TABLE 3

| Group | iv ing. 1* | po. inj.* | iv. inj. 2* |
|-------|------------|-----------|-------------|
| A | P1 | CT | EB |
| B | PBS | CT | EB |
| C | PBS | PBS | EB |

*P1(iv.) injection 1 were given in a volume of 2 ml PBS, the peroral (po.) injection were given in a volume of 5 ml, the intravenous injection 2 consisted of 1.5 ml of 3% Evans blue dissolved in PBS. Ether was used for anaesthesia during the performance of all injections.

The i.v. injection of P1 (0.5 µg) or of PBS were performed 10–15 sec before the peroral challenge with 100 µg CT or with PBS; 60 min after the peroral challenge, the rats were anaesthetised with ether and injected iv. with Evans blue. The dye was allowed to equilibrate for another 30 min, whereafter the rats were again anaesthetised with ether and perfused intracardially via the left ventricle with 250 ml of Alsevers solution/PBS=50/50, in order to remove all dye present in the vascular system. After this perfusing treatment, performed during some 2–3 min, the fluroescence registrated should represent dye present only outside the vascular system.

The brain and a part of the small intestine were sampled and frozen on dry ice and cryostat sections, 8 µm thick, were prepared. The sections were air-dried and mounted in a xylene-containing mounting media. The sections were viewed in a Zeiss fluorescence microscope, using a filter combination identical to that used for rhodamin-emitted fluorescence.

The results in FIGS. 10 and 11 demonstrate that the fluorescent intensity (white colour) is of a similar magnitude in both the small intestine (FIG. 10) and in the plexus choroideus (FIG. 11) in group A (P1 iv+CT po) and C(PBS iv+PBS po). Compared to the high fluorescent intensity in the small intestine as well as in the plexus choroideus in group B (PBS iv+CT po), the results clearly demonstrate that injection of the octapeptide prior to toxin challenge inhibits the CT-induced extravascular penetration of Evans blue. The results suggest that this holds true not only in the vascular system of the small intestine, but also in the plexus choroideus of the lateral ventricles of the brain.

In conclusion: the effect of intravenous octapeptide IVCHSKTR administration inhibits cholera toxin-induced extravascular penetration of Evans blue in the small intestine as well as in the plexus choroideus in the central nervous system. Thus, the action of rAF and its peptide derivatives is not confined to the small intestine only, but influences also the permeability of blood vessels in the central nervous system. These findings indicate that rAF and its peptide derivatives can be used to reverse pathological intracranial pressure, pressure alteration in the middle ear and various forms of permeability changes in blood vessels.

REFERENCES

[1] Young, R. A. and Davis, R. W. (1983) Proc. Natl. Acad. Sci. USA. 80, 1194–1198
[2] Sambrook, J., Fritsch, E. F., Maniatis, T. (1989) Molecular cloning: a laboratory manual, pp 1.74–1.84, Cold Spring Harbor Laboratory Press, Cold Spring Harbor, N.Y.
[3] Frohman, M. A., Dush, M. K., and Martin, G. R. (1988) Proc. Natl. Acad. Sci,. USA 86, 8998–9002.
[4] Laemmli, U. K. (1970) Nature 227,680–685.
[5] Zachrisson, G., Lagergård, T. and Lönnroth, I. (1986) Acta path. microbiol. immunol. scand. C, 94, 227–231.
[6] Chomczynski, P., Sacchi, N. (1987) Analyt. Biochem. 162, 156–159.
[7] Sambrook, J., Fritsch, E. F., Maniatis, T. (1989) Molecular cloning: a laboratory manual, pp 7.40–7.42, Cold Spring Harbor Laboratory Press, Cold Spring Harbor, N.Y.
[8] Jennische, E., Matejka, G. L. (1992) Acta Physiol. Scand. 146, 79–86.
[9] Lange, S. (1982) FEMS Microbiol. Lett. 15, 239–242.
[10] Torres, J. F., Jennische, E., Lange, S. and Lönnroth, I. (1990) Gut 781–785
[11] Lange, S., Delbro DS, Jannische E. Evans Blue permeation of intestinal mucosa in the rat. Scand J Gastroenterol 1994, 29:38–46.

FIGURE LEGENDS

FIGS. 1a–1b Nuclear acid sequence (SEQ ID NO:1) and deduced amino acid sequence (SEQ ID NO:2) of the new human protein. The confirmed amino acid sequence is underlined.

FIG. 1c. Horizontal map showing cloned cDNA and oligonucleotide primers.

FIG. 2. Coomassie brilliant blue-stained SDS-polyacrylamide minigel (A) and immunoblot probed with antisera against porcine AF (B). Lanes with unprimed numbers contain glutathione-agarose-purified GST-AF fusion proteins AF-1, AF-2 and AF-3, whereas lanes with primed numbers contain the fusion proteins cleaved with thrombin. Molecular weight references (R), (BDH), are indicated on the left. The GST-AF-1 fusion protein is highly degraded but the immunoblot analysis shows only the detection of a full-length protein and spontaneous thrombin cleavage product. There is a 26 kDa product in the GST-AF-3 protein, probably the glutathione S-transferase-tail that has been independently expressed.

FIG. 3a. Western blot using antiserum against recombinant protein AF-2. To the left, porcine (P) and three human (H1, H2, H3) pituitary glands; and to the right, the three recombinant proteins AF-1, AF-2 and AF-3 (see FIG. 2) were applied; in the centre the molecular weight standard (R).

FIG. 3b Enzyme linked immuno-assay (ELISA) of rAF using crude antiserum and affinity purified antibodies raised in rabbit.

FIG. 4. Autoradiogram of Northern blots of RNA from a human and porcine pituitary gland (p=pooled and i=individual material). Five µg of purified mRNA was applied in each basin; 3'-end $^{32}$P-labelled oligonucleotide probes were used and the autoradiogram developed after 7 days.

FIG. 5 Cryosections of adenohypophysis stained with antiserum against recombinant protein GST-AF-2. A. Sections incubated with immune serum showing scattered cells with varying degrees of positive immunoreactivity (solid arrows). Many cells completely lack staining (open arrows). B. Serial sections to A incubated with immune serum preabsorbed with excess of recombinant protein GST-AF-2. There is no specific staining of the cells. C and D. Larger magnifications of immunopositive cells demonstrating cytoplasmatic staining of the endocrine cells, n=nucleus, c=cytoplasma.

FIG. 6. Biological activity of recombinant protein AF-1 testing inhibition of cholera toxin-induced fluid secretion. Graded doses of the protein were injected intravenously in rat; three µg of cholera toxin was injected into an intestinal loop; after five hours the accumulated fluid (mg/cm intestine) in the loop was measured. Each value represents the mean±S.A.E. of a group of six animals.

FIG. 7. Biological activity of intravenously injected rAF-1; 0.5 µg of rAF was administered 20–30 sec before or 90 min after challenge with 3 µg of cholera toxin in an intestinal loop of rat.

FIG. 8. Biological activity of intraluminarly injected rAF-1; 3 µg of rAF was injected 20–30 sec before or 90 min after challenge with 3 µg of cholera toxin in an intestinal loop of rat; the rAF was injected about 5 cm proximate to the loop in which the toxin was injected.

FIGS. 9A–F. A (×2.5) is control (PBS) loops showing cellular debris in the intestinal lumen (L), but no staining of the remaining mucosa, which suggests a total destruction of the epithelial lining. B (0.5 µl of P1 prior to toxin challenge) shows a clearly delineated epithelial lining forming villi, suggesting a conserved and normal intestinal mucosa. L=intestinal lumen. Bars=500 µm. C (×10) shows the destructed mucosa in the PBS-treated control group, and D shows the corresponding mucosa in the experimental (P1-treated) group. The black arrow point at the epithelial lining, LP=lamina propria, mm=muscularis mucosa, open arrow point at the crypt cells. Bars=100 µm. E (×25) shows the destructed mucosa in the control (PBS-treated) group, and F shows a corresponding magnification from a rat subjected to P1 treatment prior to toxin challenge. Bars=50 µm.

FIGS. 10A–C. Evans blue fluorescence in jejunal specimens from three groups of rats treated with cholera toxin (CT) or control buffer (PBS); pretreatment with antisecretory peptide P1 or control buffer (PBS). LP=lamina propria. Black arrow indicating epithelial cell lining; open arrow head indicating crypt cells. Bars=100 µm.

FIG. 11 Evans blue fluorescence in plexus choroideus specimens from the rats shown in FIGS. 10A–C. Bars=50 µm.

What is claimed is:

1. An isolated recombinant polypeptide comprising SEQ ID NO:2 or a homolog or a fragment thereof, and wherein said homolog or fragment of SEQ ID NO:2 comprises formula $X_1VCX_2X_3KX_4R$, (a) wherein said formula corresponds to amino acids 35–42 of SEQ ID NO:2;

(b) $X_1$ is I or is absent;

(c) $X_2$ is H, R or K;

(d) $X_3$ is S, L or anther neutral amino acid; and (d) $X_4$ is T or A; and wherein said recombinant polypeptide or homolog or fragment thereof has antisecretory activity when administered after cholera toxin challenge.

2. A composition comprising the recombinant polypeptide or homolog or fragment of claim 1.

3. The recombinant polypeptide of claim 1, wherein the recombinant protein or homolog or fragment is derived from a bacterium, a yeast, a plant or a vertebrate except for human.

4. The recombinant polypeptide of claim 1, wherein said recombinant protein consists of SEQ ID NO:2.

5. A composition comprising the recombinant polypeptide of claim 4.

6. A composition for use in vertebrates including humans comprising an effective amount of the recombinant polypeptide or fragment or homolog of claim 1, wherein said composition has antisecretory activity.

7. A method of using a recombinant protein or homolog or fragment of claim 1 comprising administering an effective amount of the recombinant polypeptide or homolog or fragment to a vertebrate to induce antisecretory activity.

8. A method of inhibiting diarrhea in a vertebrate comprising administering the composition of claim 2.

9. The method of claim 8, wherein said vertebrate is a human.

10. A feed or food for vertebrates including humans comprising an active agent, wherein the active agent is a recombinant polypeptide or a homolog or a fragment thereof of claim 1 wherein said feed or food has antisecretory activity.

11. The feed or food of claim 10, wherein the recombinant polypeptide or homolog or fragment is derived from bacteria, yeast or plants.

12. A feed additive comprising the recombinant polypeptide or homolog or fragment thereof of claim 1 wherein said feed additive has antisecretory activity.

13. An isolated recombinant polypeptide comprising (a) amino acids 35–42, (b) amino acids 35–46, (c) amino acids 36–51, (d) amino acids 36–80, or (e) amino acids 1–80 of SEQ ID NO:2 or (f) a polypeptide of formula $X_1VCX_2X_3KX_4R$ wherein the formula corresponds to amino acids 35–42 of SEQ ID NO:2 of any of the polypeptides (a) to (e), wherein (i) $X_1$ is I or is absent;

(ii) $X_2$ is R, R, or K;

(iii) $X_3$ is S, L, or another neutral amino acid; and (iv) $X_4$ is T or A, wherein said recombinant polypeptide has antisecretory activity when administered after cholera toxin challenge.

14. A composition comprising the polypeptide of claim 13.

15. The polypeptide of claim 13, wherein the polypeptide is derived from a bacterium, a yeast, a plant or a vertebrate except for human.

16. A composition for use in vertebrates including humans comprising an effective amount of the polypeptide of claim 13, wherein said composition has antisecretory activity.

17. A method of using the polypeptide of claim 13 comprising administering an effective amount of the polypeptide to a vertebrate to induce antisecretory activity.

18. A method of inhibiting diarrhea in a vertebrate comprising administering the composition of claim 14.

19. The method of claim 18, wherein said vertebrate is a human.

20. A feed or food for vertebrates comprising an active agent, wherein said active agent is the polypeptide of claim 13 wherein said feed or food has antisecretory activity.

21. The feed or food of claim 20, wherein the polypeptide is derived from bacteria, yeast or plants.

22. A feed additive comprising the polypeptide of claim 13 wherein said feed additive has antisecretory activity.

23. An isolated recombinant polypeptide consisting of amino acids selected from the group consisting of (a) amino acids 35–42, (b) amino acids 35–46, (c) amino acids 36–51, (d) amino acids 36–80, or (e) amino acids 1–80 of SEQ ID NO:2, wherein said recombinant polypeptide has antisecretory activity when administered after cholera toxin challenge.

* * * * *